US011389172B2

(12) United States Patent
Friedman et al.

(10) Patent No.: US 11,389,172 B2
(45) Date of Patent: Jul. 19, 2022

(54) ROTATIONALLY TORQUABLE ENDOVASCULAR DEVICE WITH VARIABLE FLEXIBILITY TIP

(71) Applicant: RAPID MEDICAL LTD., Yokneam (IL)

(72) Inventors: Aharon Friedman, Haifa (IL); Matan Gedulter, Givat Ela (IL); Ronen Eckhouse, Shimshit (IL); Moshe Miller, Jerusalem (IL)

(73) Assignee: Rapid Medical LTD., Yokneam (IL)

( * ) Notice: Subject to any disclaimer, the term of this patent is extended or adjusted under 35 U.S.C. 154(b) by 0 days.

(21) Appl. No.: 16/668,427

(22) Filed: Oct. 30, 2019

(65) Prior Publication Data
US 2020/0060683 A1    Feb. 27, 2020

Related U.S. Application Data

(63) Continuation-in-part of application No. 16/388,056, filed on Apr. 18, 2019, now Pat. No. 11,090,464, (Continued)

(51) Int. Cl.
*A61B 17/12* (2006.01)
*A61B 17/00* (2006.01)

(52) U.S. Cl.
CPC .... *A61B 17/1214* (2013.01); *A61B 17/00234* (2013.01); *A61B 2017/003* (2013.01); (Continued)

(58) Field of Classification Search
CPC .......... A61B 17/1214; A61B 17/00234; A61B 2017/003; A61M 25/09; A61M 25/0053; A61F 2/95; A61L 31/022
See application file for complete search history.

(56) References Cited

U.S. PATENT DOCUMENTS 3,773,034 A    11/1973 Burns et al.
4,815,478 A    3/1989 Buchbinder et al.
(Continued)

FOREIGN PATENT DOCUMENTS

WO    WO 2018/060776 A2    4/2018
WO    WO 2019/116102 A2    6/2019

OTHER PUBLICATIONS

International Search Report and Written Opinion of the International Searching Authority dated Jul. 10, 2018, in International Application No. PCT/IB2017/001663 (10 pages).
(Continued)

*Primary Examiner* — Patrick Fernandes
(74) *Attorney, Agent, or Firm* — Finnegan, Henderson, Farabow, Garrett & Dunner LLP

(57) ABSTRACT

Endovascular and intravascular devices and methods of manufacturing endovascular and intravascular devices may be provided. In one implementation, an intravascular device including an elongated sheath and an elongated coil distal to the sheath may be provided. The coil may include a first coil segment formed from a plurality of wires helically-wound at a first coil angle; a second coil segment formed from a first subset of the plurality of wires that is helically-wound at a second coil angle that is different from the first coil angle; and a third coil segment formed from a second subset of the plurality of wires that is helically-wound at a third coil angle that is different from the first and second coil angles. The coil segments may be configured such that flexibility of the coil increases in a longitudinal direction toward the distal end of the coil.

19 Claims, 20 Drawing Sheets

Related U.S. Application Data which is a continuation-in-part of application No. PCT/IB2017/001663, filed on Sep. 28, 2017.

(60) Provisional application No. 62/401,387, filed on Sep. 29, 2016.

(52) U.S. Cl.
CPC ............... *A61B 2017/00867* (2013.01); *A61B 2017/1205* (2013.01)

(56) References Cited

U.S. PATENT DOCUMENTS

| | | | |
|---|---|---|---|
| 4,827,941 A | 5/1989 | Taylor et al. | |
| 4,940,062 A | 7/1990 | Hampton et al. | |
| 5,318,529 A | 6/1994 | Kontos | |
| 5,484,409 A | 1/1996 | Atkinson et al. | |
| 2003/0069521 A1* | 4/2003 | Reynolds | A61L 31/022 600/585 |
| 2003/0181827 A1 | 9/2003 | Hojeibane et al. | |
| 2006/0074478 A1* | 4/2006 | Feller, III | A61F 2/95 623/1.11 |
| 2006/0089618 A1* | 4/2006 | McFerran | A61M 25/0053 604/525 |
| 2006/0200047 A1 | 9/2006 | Galdonik et al. | |
| 2010/0004722 A1 | 1/2010 | Täubert et al. | |
| 2010/0249773 A1 | 9/2010 | Clark et al. | |
| 2010/0305475 A1 | 12/2010 | Hinchliffe et al. | |
| 2011/0144538 A1* | 6/2011 | Shimogami | A61M 25/09 600/585 |
| 2014/0343457 A1 | 11/2014 | Shekalim et al. | |
| 2014/0350568 A1 | 11/2014 | Shekalim et al. | |
| 2017/0209671 A1 | 7/2017 | Ring | |
| 2018/0015260 A1 | 1/2018 | Sano et al. | |
| 2019/0240457 A1 | 8/2019 | Sudin et al. | |

OTHER PUBLICATIONS

International Search Report and Written Opinion of the International Searching Authority dated May 31, 2019, in International Application No. PCT/IB2018/001571 (6 pages).

U.S. Appl. No. 16/668,248; Intraluminal Device With Looped Core Wire; Aharon Friedman et al; filed Oct. 30, 2019.

International Search Report and Written Opinion of the International Searching Authority dated Jul. 31, 2020, by the U.S. Patent and Trademark Office in corresponding International Application No. PCT/IB2020/000284 (9 pages).

* cited by examiner

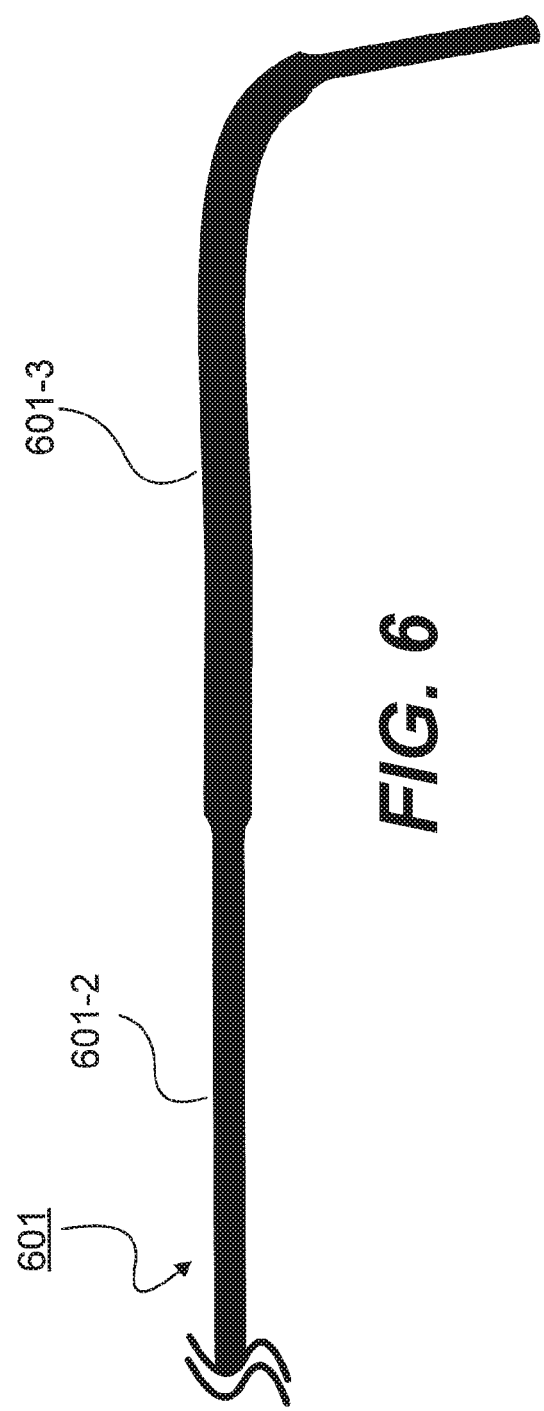

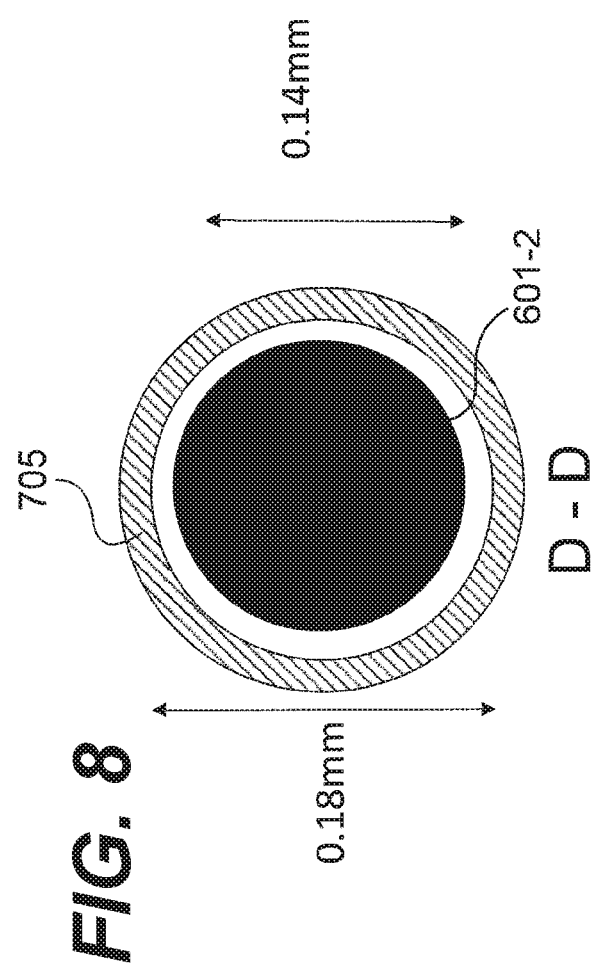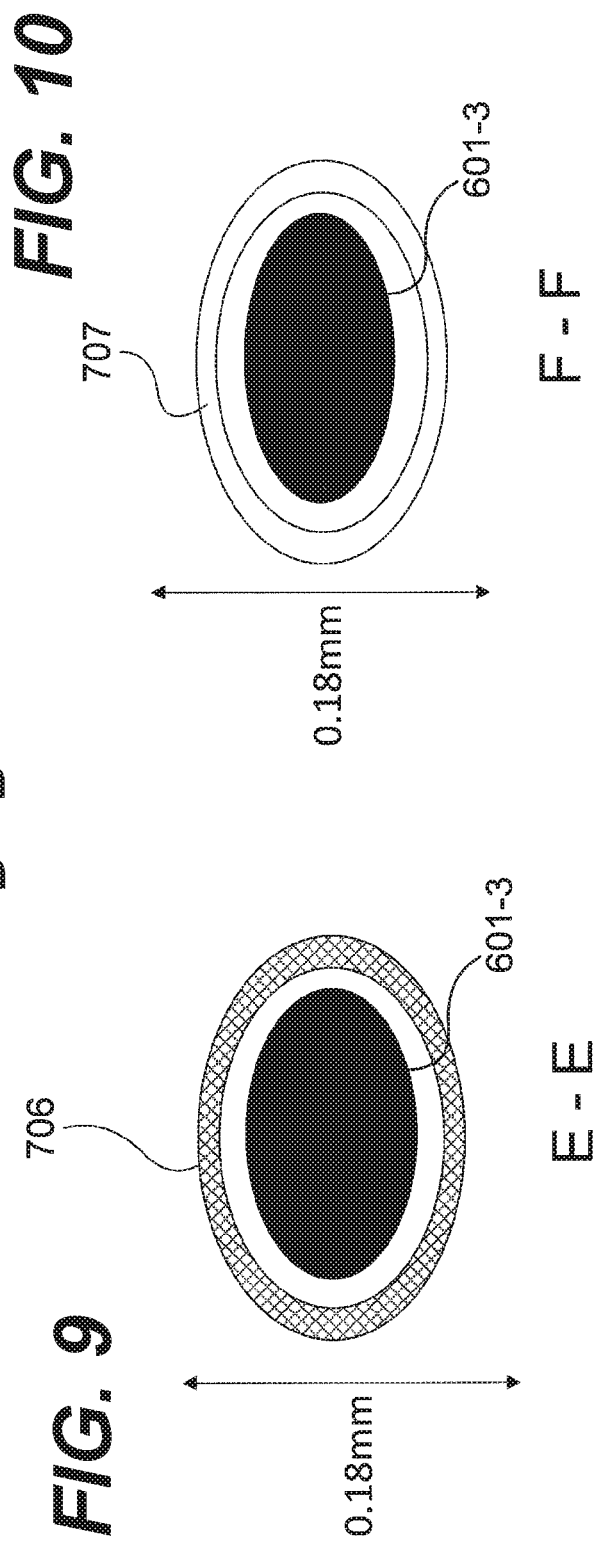

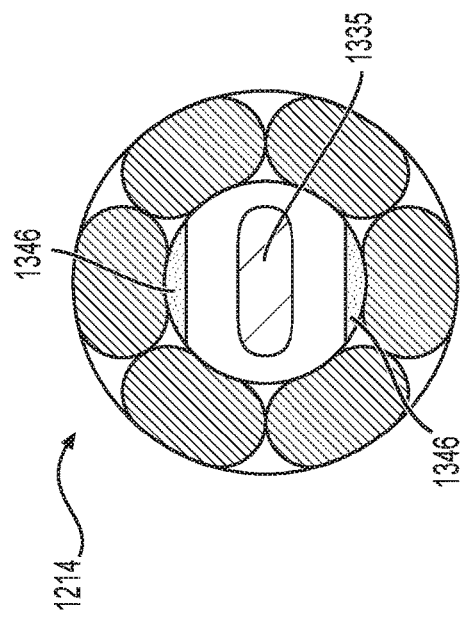
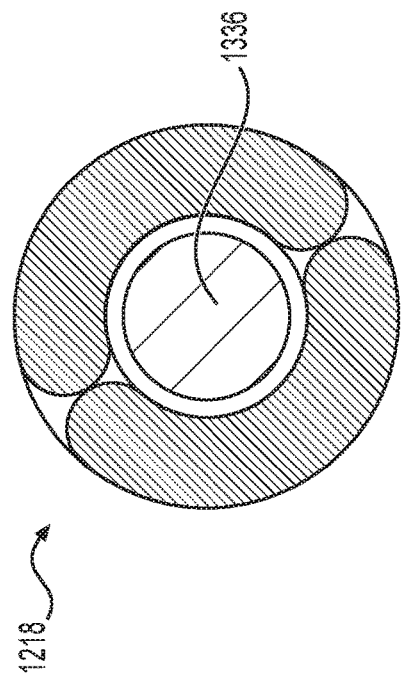
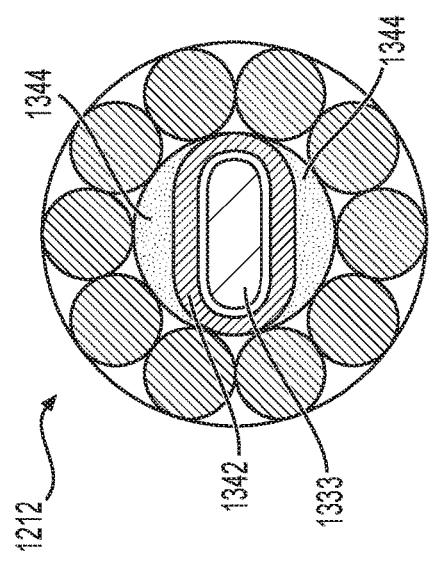
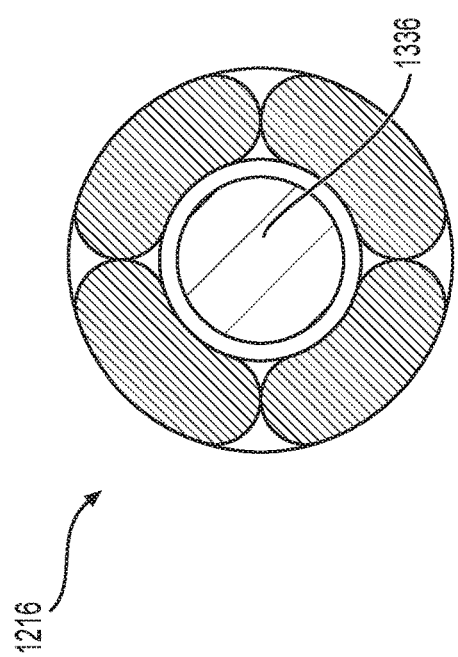

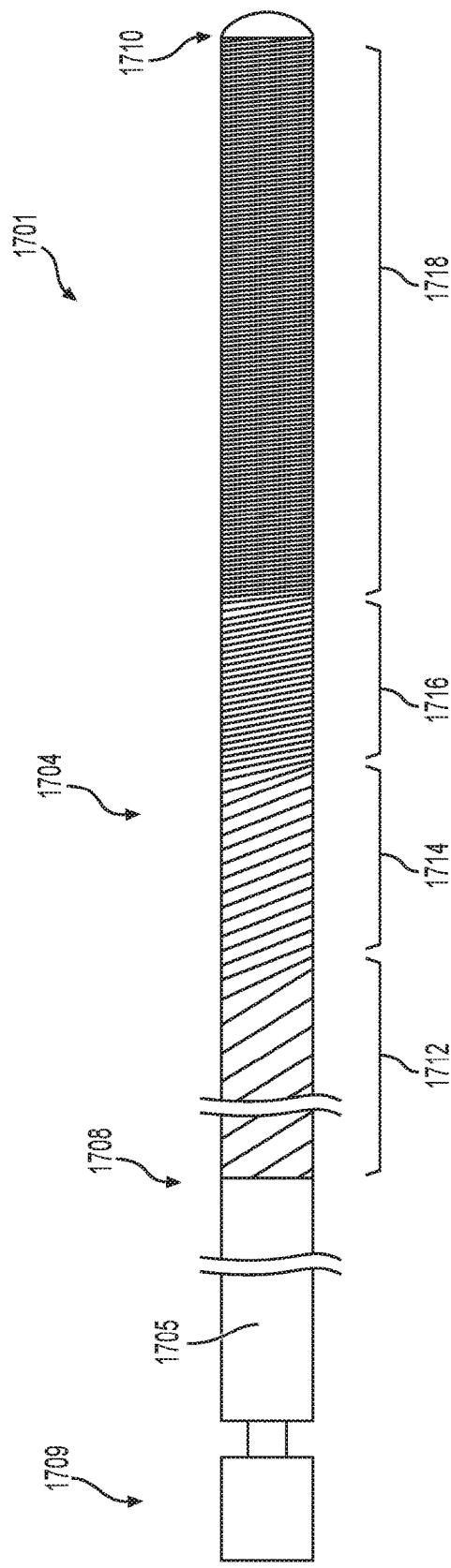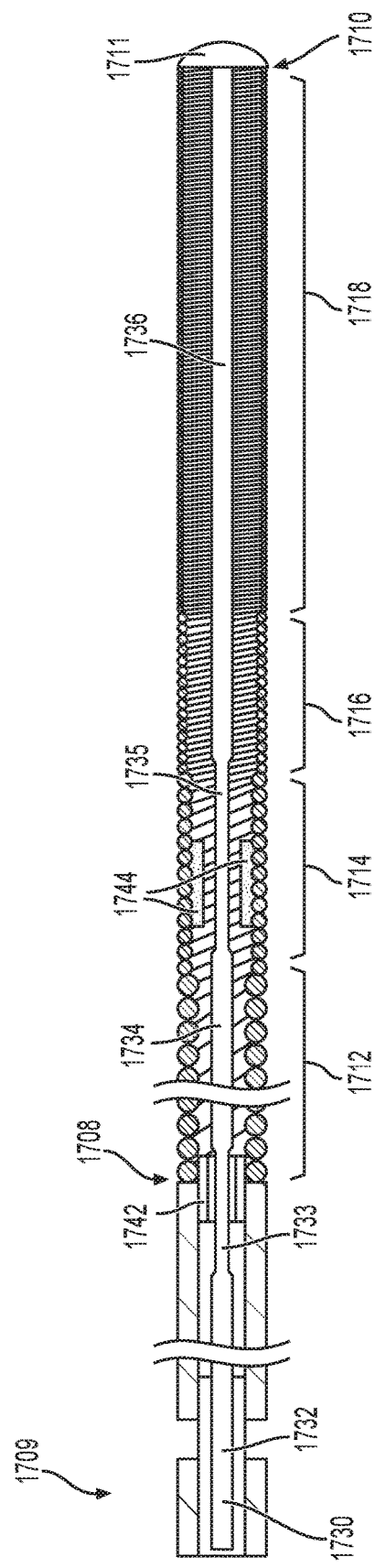

ROTATIONALLY TORQUABLE ENDOVASCULAR DEVICE WITH VARIABLE FLEXIBILITY TIP

CROSS-REFERENCES TO RELATED APPLICATIONS

This application is a Continuation-In-Part of U.S. application Ser. No. 16/388,056, filed Apr. 18, 2019, which is a Continuation-In-Part of International Application No. PCT/IB2017/001663, filed Sep. 28, 2017, which claims the benefit of priority from U.S. Provisional Application No. 62/401,387 filed Sep. 29, 2016, all of which are herein incorporated by reference in their entireties.

TECHNICAL FIELD

This disclosure relates generally to endovascular devices. In particular, the disclosure relates generally to an exemplary endovascular device including a coil formed by a plurality of wound wires that is configured such that flexibility of the coil increases in a longitudinal direction toward the distal end of the endovascular device.

SUMMARY

Embodiments of the present disclosure may include an intravascular device having an elongated sheath. The elongated sheath may include a proximal end and a distal end, the elongated sheath being sized and configured to traverse human vasculature. The intravascular device may also include an elongated coil secured relative to the distal end of the elongated sheath. The elongated coil may extend between a proximal end of the coil and a distal end of the coil to define a longitudinal axis. The elongated coil may include a first coil segment formed from a plurality of wires. The wires of the first coil segment may be helically-wound in the first coil segment at a first coil angle relative to the longitudinal axis. The elongated coil may also include a second coil segment distal to the first coil segment. The second coil segment may be formed from a first subset of the plurality of wires. The first subset of wires may be helically-wound in the second coil segment at a second coil angle that is different from the first coil angle. The elongated coil may also include a third coil segment distal to the second coil segment. The third coil segment may be formed from a second subset of the plurality of wires. The second subset of wires may be helically-wound in the third coil segment at a third coil angle that is different from the first coil angle and the second coil angle. The coil segments of the elongated coil may be configured such that flexibility of the elongated coil increases in a longitudinal direction toward the distal end of the elongated coil.

The plurality of wires may include between six wires and 16 wires, the first subset of wires may include between three wires and eight wires, and the second subset of wires may include one wire or two wires. The plurality of wires may include ten wires, the first subset of wires may include four wires, and the second subset of wires may include two wires. The second coil angle may be larger than the first coil angle and may be smaller than the third coil angle. The first coil angle may be between 55° and 65°, the second coil angle may be between 65° and 75°, and the third coil angle may be between 75° and 85°. The wires of the second subset of wires may be constructed at least partially of a first material and the remaining wires of the plurality of wires may be constructed of a second material that is different from the first material. Wires extending to the distal end of the elongated coil may be constructed at least partially from the first material. At least one wire of the plurality of wires may include a distal end that is situated proximally from the distal end of the elongated coil.

The intravascular device may additionally include a fourth coil segment situated between the first coil segment and the second coil segment. The fourth coil segment may be formed from a third subset of the plurality of wires that includes more wires than the first and second subsets of wires. The third subset of wires may be helically-wound in the fourth coil segment at a fourth coil angle that is larger than the first coil angle and smaller than the second coil angle. The third subset of wires may include between four wires and nine wires. The third subset of wires may include six wires. The third coil segment may have a greater axial length than the second coil segment and the fourth coil segment. The fourth coil angle may be between 55° and 65°. Spaces may be formed between windings of the elongated coil in a first region of the elongated coil. The first region of the elongated coil may be situated within the third coil segment and may extend axially to the distal end of the elongated coil. The spaces between the windings may be spaced at a regular interval between windings. A wire gauge of the elongated coil may decrease toward the distal end of the elongated coil. Material composition of the elongated sheath may vary toward the distal end of the elongated sheath. The elongated sheath may be constructed of at least one of a metal, a nickel-titanium alloy, or a synthetic material.

The intravascular device may additionally include an elongated core wire arranged at least partially within the sheath. The elongated core wire may be configured such that when the core wire is moved axially, the distal end of the elongated coil may bend radially. The core wire may be doubled back in a loop within the elongated coil such that a terminal distal end of the core wire may be spaced from the distal end of the elongated coil. The intravascular device may additionally include a movement restrictor situated at least partially within the elongated coil. The movement restrictor may be configured to limit axial movement of the terminal distal end of the core wire in at least one axial direction relative to the elongated coil and to permit the loop of the core wire to buckle, resulting in a bend in the distal end of the elongated coil, when an axial force is exerted on the core wire. The coil segments of the elongated coil may be configured to have differing flexibilities. The coil segments of the elongated coil may be aligned axially along the elongated coil to form a unified structure of the elongated coil that may have axially variable flexibility.

BRIEF DESCRIPTION OF THE DRAWINGS

The accompanying drawings, which are incorporated in and constitute a part of this specification, illustrate disclosed embodiments and, together with the description, serve to explain the disclosed embodiments.

FIG. 6 illustrates a control wire for another exemplary endovascular device, consistent with various embodiments of the present disclosure.

FIG. 8 illustrates an inner cross-section of a section of the exemplary endovascular device of FIG. 7, consistent with various embodiments of the present disclosure.

FIG. 9 illustrates an inner cross-section of a second section of the exemplary endovascular device of FIG. 7, consistent with various embodiments of the present disclosure.

FIG. 10 illustrates an inner cross-section of a third section of the exemplary endovascular device of FIG. 7, consistent with various embodiments of the present disclosure.

FIGS. 13B-13E illustrate cross-sectional views of the exemplary endovascular device of FIG. 12A, consistent with various embodiments of the present disclosure.

FIG. 17A illustrates an exemplary endovascular device, consistent with various embodiments of the present disclosure.

FIG. 17B illustrates an interior view of the exemplary endovascular device of FIG. 17A, consistent with various embodiments of the present disclosure.

Annotations appearing in the figures are exemplary only, and are not restrictive of the invention as claimed.

DETAILED DESCRIPTION OF EMBODIMENTS

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Figure 1:
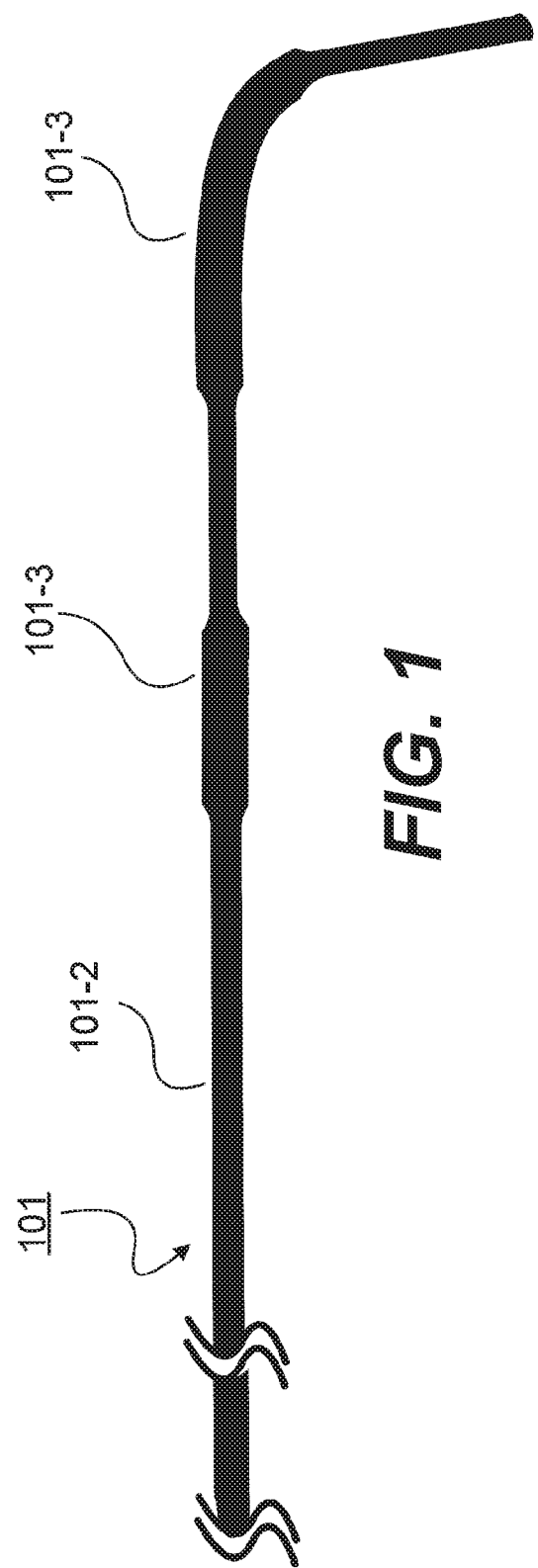
FIG. 1 illustrates a control wire for an exemplary endovascular device, consistent with various embodiments of the present disclosure.
Figure 2:
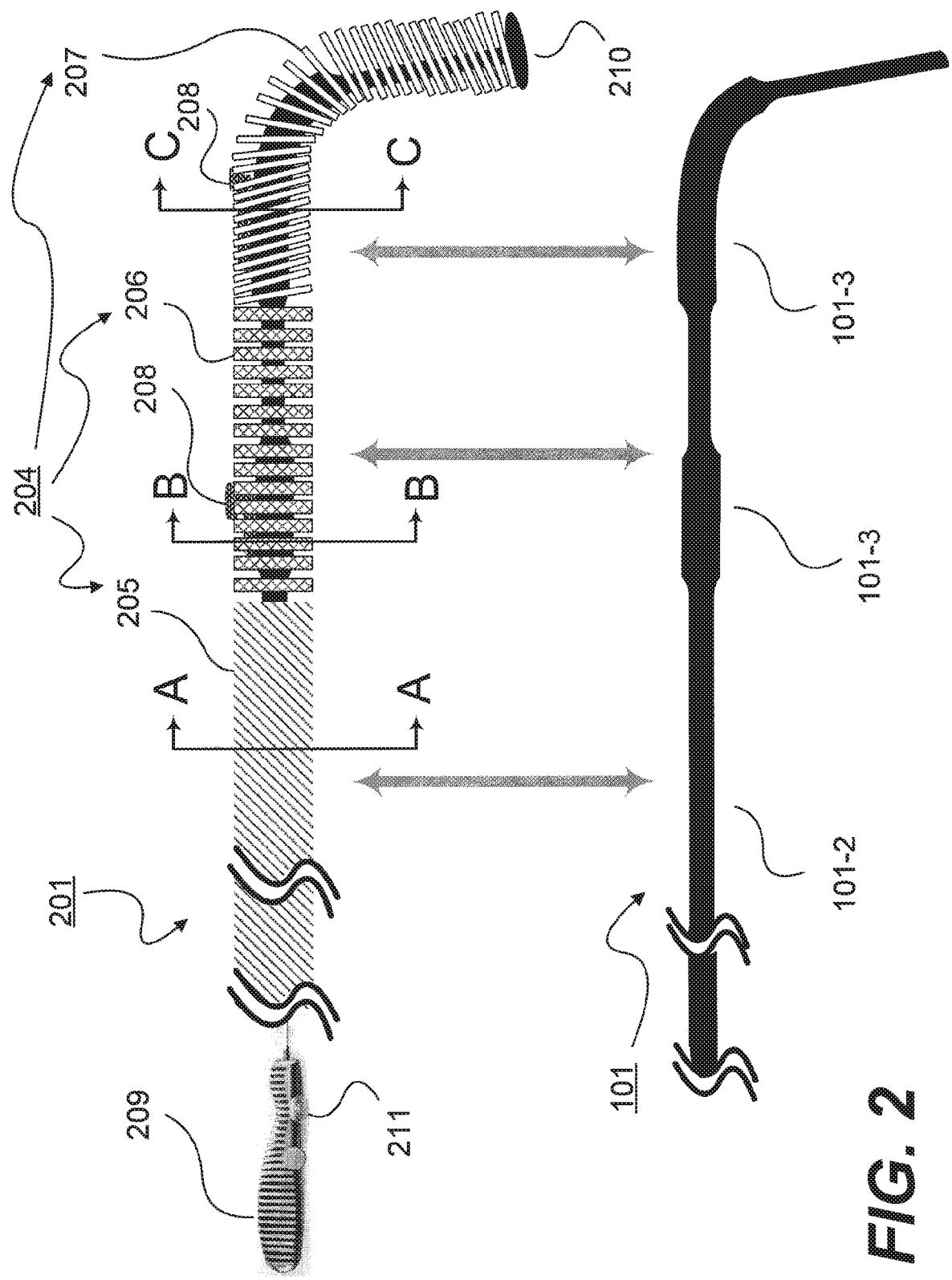
FIG. 2 illustrates an exemplary endovascular device with the control wire of FIG. 1, consistent with various embodiments of the present disclosure.

FIG. 1 illustrates a control wire 101 of an exemplary endovascular device in accordance with the disclosure, which may be deformed or flattened in two zones 101-3, and may be round in other areas along its axis 101-2. FIG. 2 illustrates an exemplary endovascular device 201 using control wire 101 in accordance with the disclosure. (Solely to illustrate the position of zones 101-2 and 101-3 in endovascular device 201, with the understanding that control wire 101 is part of endovascular device 201, FIG. 2 also separately depicts control wire 101 of FIG. 1, with zones 101-3 and 101-2 generally aligned to endovascular device 201.) As shown in FIG. 2, endovascular device 201 may include an elongated shaft 204 which may include a tube 205, a cable of wires 206, and a single wire coil 207. A distal tip 210 of the elongated shaft 204 may be attached to control wire 101, for example. At a proximal end of the elongated shaft 204, the control wire 101 may be connected to a slider 211 of a handle 209, with the elongated shaft 204 connected to the handle 209 to facilitate the relative movement. (In FIG. 2, handle 209 is not depicted to the same scale as that of elongated shaft 204.) In accordance with at least some embodiments, two polymers 208 may be inserted between the elongated shaft 204 and the control wire 101 to prevent the radial movement between the control wire 101 and the elongated shaft 204.

Consistent with the embodiment shown in FIGS. 9 and 10, in at least some embodiments of an exemplary endovascular device of the disclosure, the cable of wires 206 and the single wire coil 207 of the elongated shaft 204 may be elliptical. This elliptical shape resists relative rotation of the elongated shaft 204 and the control wire 101, enabling torqueing of the device. Alternatively, other non-symmetrical shapes (e.g., cross-sections) may be employed, consistent with the present disclosure to resist rotation and to permit torqueing.

At least some embodiments of an exemplary endovascular device of the disclosure may encompass a fixture enabling transmission of a radial force of the elongated shaft 204 to the control wire 101 with 1:1 ratio. This may be achieved, for example, by preventing axial rotation between the control wire 101 and the elongated shaft 204 without preventing the axial movement between the control wire 101 and the elongated shaft 204. And such axial rotation prevention (without axial movement prevention) may be achieved, for example, by deforming at least a portion of the control wire 101 and making at least a portion of the inner cross-section of the round elongated shaft 204 non-round respectively. For example, there may be an overlap between the two rectangular (or flattened) portions 101-3 even during axial movement of the control wire 101 compared to the elongated shaft 204.

A control wire 101 with at least some flat or rectangular section or sections may be achieved by, for example, selectively pressing the control wire 101, by adhesion of additional materials to form a non-round shape, or by other means.

Achieving a non-round inner cross-section may be achieved, for example, by attaching rectangular shaped materials 208 to an inner wall of the elongated shaft 204. As another example, a polymer 208 may be inserted through the wire cable to create a non-round cross-section. The polymer 208 may be heated and inserted through holes in the wall of the elongated shaft 204 and shaped as needed by a rectangular mandrel.

Figure 3:
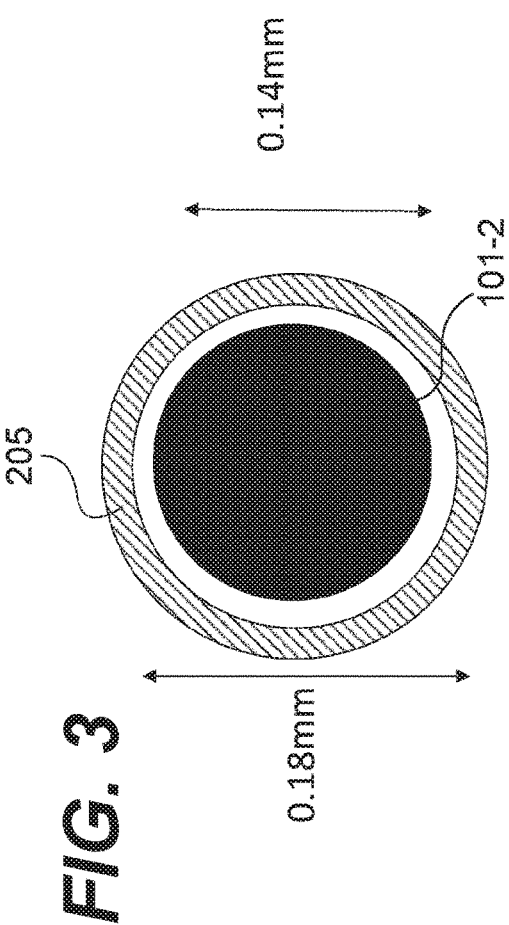
FIG. 3 illustrates an inner cross-section of a section of the exemplary endovascular device of FIG. 2, consistent with various embodiments of the present disclosure.

As shown in FIG. 3, which illustrates an inner cross-section A-A of a section of exemplary endovascular device 201, the control wire 101 may be made from 0.14 mm Nitinol wire. A distal tip of the wire 101 may be gradually grinded to an outer diameter of about 70 µm. The elongated shaft 204 may be made from a 130 cm Nitinol tube with an inner diameter of 0.18 mm which may be bonded to a PTFE covered cable of ten 70 µm Nitinol wires and the distal section may be a single 70 µm wire which may be coiled.

Figure 4:
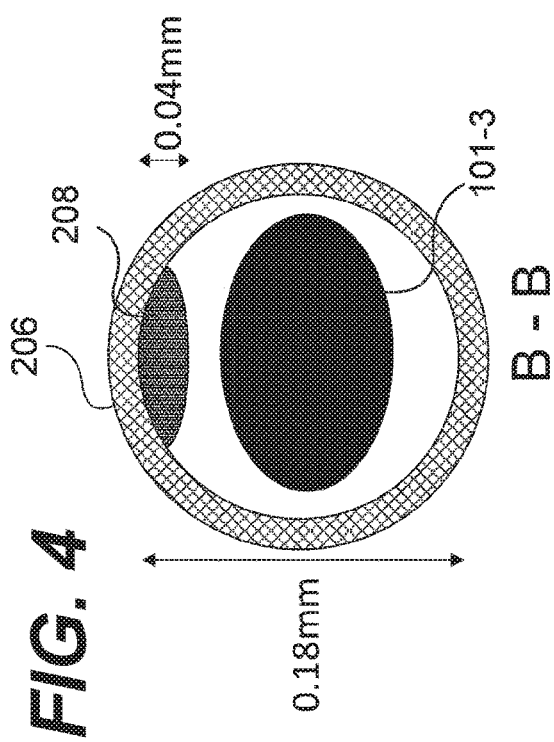
FIG. 4 illustrates an inner cross-section of a second section of the exemplary endovascular device of FIG. 2, consistent with various embodiments of the present disclosure.

As shown in FIG. 4, which illustrates an inner cross-section B-B of a section of exemplary endovascular device 201, the control wire 101 may be pressed to create flat sections 101-3 of about 0.16 mm×0.12 mm of 30 mm of length. Using a rectangular mandrel, a polymer 208 may be inserted through the wire cable 206 to create a non-round cross-section in areas that overlap the non-round sections of the control wire 101. As a result, relative axial movement between the control wire 101 and the elongated shaft 204 may be maintained while the axial rotation between the control wire 101 and the elongated shaft 204 (which includes cable 206) may be prevented.

Figure 5:
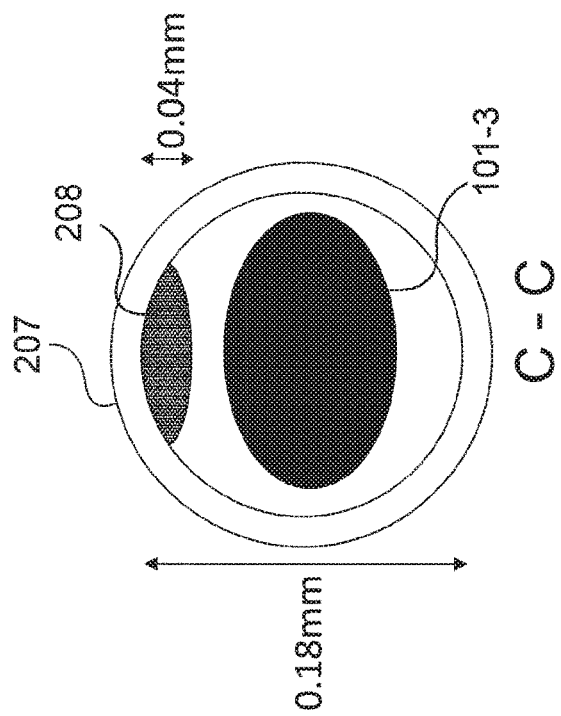
FIG. 5 illustrates an inner cross-section of a third section of the exemplary endovascular device of FIG. 2, consistent with various embodiments of the present disclosure.

FIG. 5 illustrates an inner cross-section C-C of a section of exemplary endovascular device 201, similar to cross-section B-B of FIG. 4. Again, as a result, relative axial movement between the control wire 101 and the elongated shaft 204 may be maintained while the axial rotation between the control wire 101 and the elongated shaft 204 (which includes single wire coil 207) may be prevented.

Figure 7:
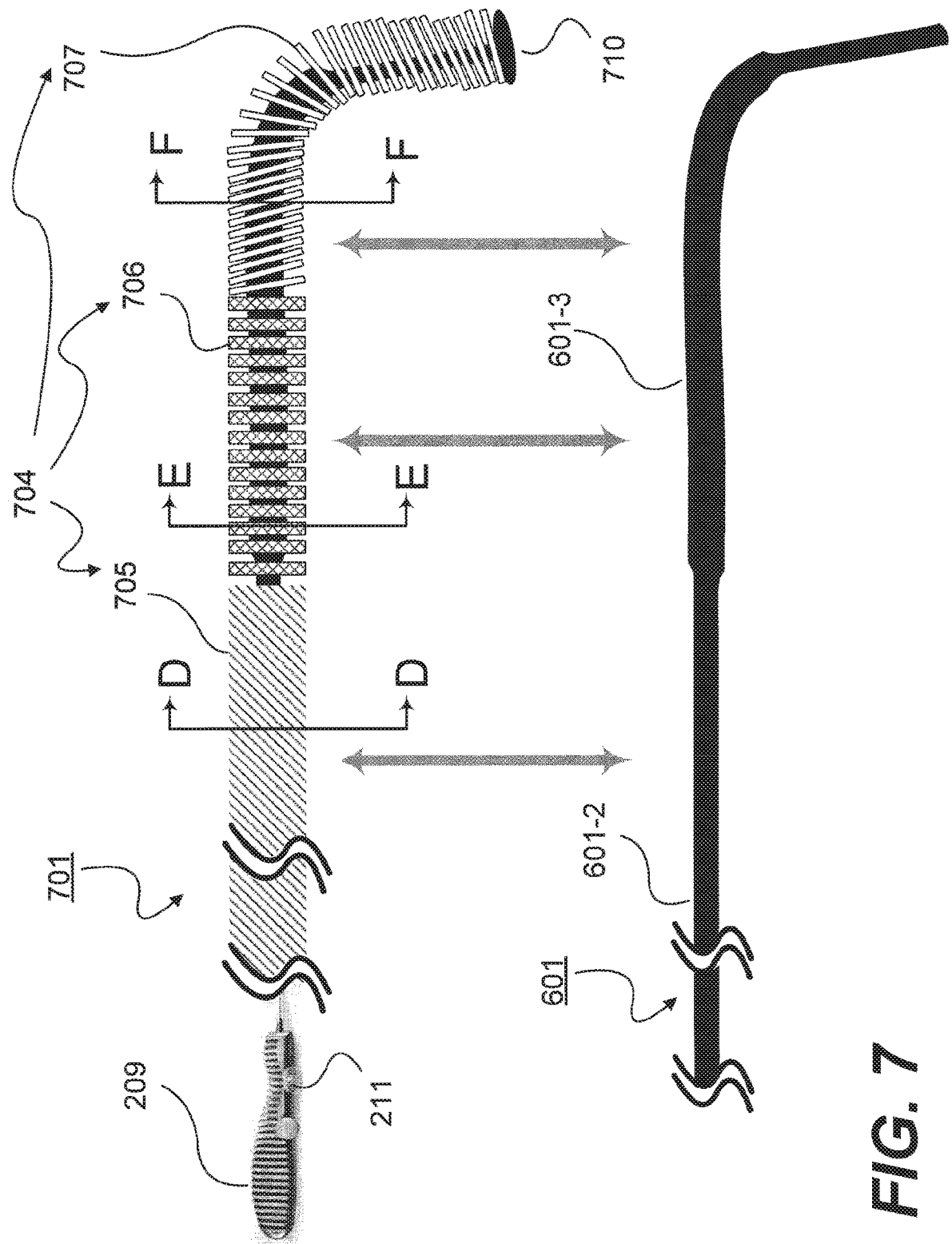
FIG. 7 illustrates an exemplary endovascular device with the control wire of FIG. 6, consistent with various embodiments of the present disclosure.

In a further embodiment, FIG. 6 illustrates a control wire 601 of an exemplary endovascular device in accordance with the disclosure, which may be deformed or flattened in zone 601-3, and may be round in other areas along its axis 601-2. FIG. 7 illustrates an exemplary endovascular device 701 using control wire 601 in accordance with the disclosure. (Solely to illustrate the position of zones 601-2 and 601-3 in endovascular device 701, with the understanding that control wire 601 is part of endovascular device 701, FIG. 7 also separately depicts control wire 601 of FIG. 6, with zones 601-3 and 601-2 generally aligned to endovascular device 701.) As shown in FIG. 7, endovascular device 701 may include an elongated shaft 704 which may include a tube 705, a cable of wires 706, and a single wire coil 707. A distal tip 710 of the elongated shaft 704 may be attached to control wire 601, for example. At a proximal end of the elongated shaft 704, the control wire 601 may be connected to a slider 211 of a handle 209, with the elongated shaft 704 connected to the handle 209 to facilitate the relative movement. (In FIG. 7, handle 209 is not depicted to the same scale as that of elongated shaft 704.)

FIG. 8 illustrates an inner cross-section D-D of a section of exemplary endovascular device 701. The control wire 601 may be made from 0.14 mm Nitinol wire. A distal tip of the wire 601 may be gradually grinded to an outer diameter of about 70 µm. The elongated shaft 704 may be made from a 130 cm Nitinol tube with an inner diameter of 0.18 mm which may be bonded to a PTFE covered cable of ten 70 µm Nitinol wires and the distal section may be a single 70 µm wire which may be coiled.

As shown in FIGS. 9 and 10, which illustrates inner cross-sections E-E and F-F of a section of exemplary endovascular device 701, the control wire 601 may be pressed to create flat sections 101-3 of about 0.16 mm×0.12 mm of 30 mm of length. As mentioned above, in FIGS. 9 and 10, the cable of wires 706 and the single wire coil 707 of the elongated shaft 704 may be elliptical. This elliptical shape resists relative rotation of the elongated shaft 704 and the control wire 601, enabling torqueing of the device. Alternatively, other non-symmetrical shapes (e.g., cross-sections) may be employed, consistent with the present disclosure to resist rotation and to permit torqueing.

In other embodiments, a single wire coil may be provided, extending from a multi-wire cable with a control wire that runs through the core of both. This enables the control wire to steer the more flexible coiled end of the coil, without causing the multi-wire cable to appreciably bend.

Figure 11A:
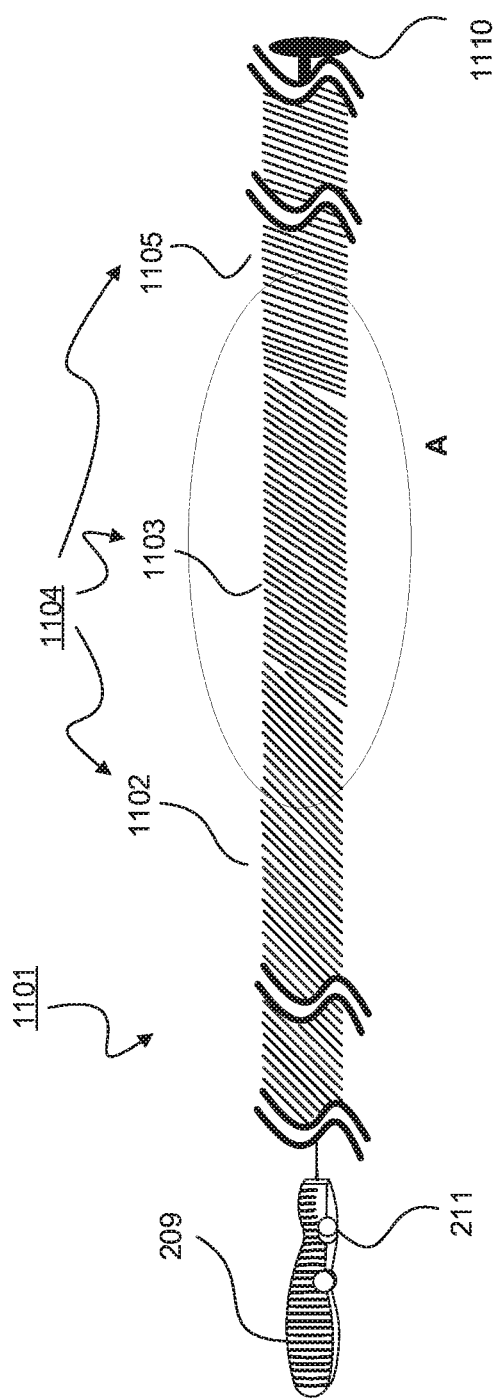
FIG. 11A illustrates an exemplary endovascular device, consistent with various embodiments of the present disclosure.

FIG. 11A illustrates an exemplary endovascular device 1101, according to various embodiments of the present disclosure. As shown in FIG. 11A, endovascular device 1101 may include an elongated shaft 1104, which may include a cable of wires, including a proximal segment 1102, at least one transition segment 1103, and a distal segment 1105. A distal tip 1110 of the elongated shaft 1104 may be attached to control wire 101 (as shown in FIG. 1), for example. At a proximal end of the elongated shaft 1104, the control wire 101 may be connected to a slider 211 of a handle 209, with the elongated shaft 1104 connected to the handle 209 to facilitate the relative movement. (In FIG. 11A, handle 209 is not depicted to the same scale as that of elongated shaft 1104.)

Hollow shaft 1104 may include a tube (for example, tube 205 of FIG. 2 or tube 705 of FIG. 7), and the cable of wires may be connected to a distal end of the tube (not shown). The cable may include a proximal segment 1102, at least one transition segment 1103, and a distal segment 1105. Proximal segment 1102 may be configured to transfer torque. In some embodiments, for example, a torque device, such as a torquer, may be threaded over the proximal end of the elongated shaft 1104 and tightened over the proximal end of the elongated shaft 1104. A rotational force exerted on the proximal end of the elongated shaft 1104, using the torquer, may cause a rotational force to be applied to a working element located proximate the distal end of the elongated shaft 1104. The ratio of the rotational force exerted on the proximal end of the elongated shaft 1104 to the rotational force applied to the working element may be approximately 1:1. The position of the torquer over the elongated shaft 1104 may be adjusted.

In some embodiments, proximal segment 1102 may be more rigid, compared to at least one transition segment 1103 and distal segment 1105, such that proximal segment 1102 may be configured to transfer torque. Proximal segment 1102 may be formed of a first number of wires, and the first number of wires required to form proximal segment 1102 may be based on certain constraints. For example, certain constraints may include an outer diameter of the cable, an inner diameter of the cable, or an optimal cable angle for torque transfer. In some embodiments, proximal segment 1102 may be formed of about five to 20 wires. For example, proximal segment 1102 may be formed of about nine wires. In another example, proximal segment 1102 may be formed of about ten wires.

The cable may further include at least one transition segment 1103 adjacent to the proximal segment 1102. Transition segment 1103 may be configured to provide a gradual transition between the proximal segment 1102 and a distal segment 1105. In some embodiments, the cable may include about one to ten transition segments 1103. For example, the cable may include about two transition segments 1103. The number of transition segments 1103 may vary based on various parameters, including rigidity of proximal segment 1102, flexibility of distal segment 1105, length of the elongated shaft 1104, a length of the cable, or number of wires used to form the cable. Transition segment 1103 may be formed of about two to 19 wires. For example, transition segment 1103 may be formed of about three to six wires. If the cable includes more than one transition segment 1103, the number of wires used to form each transition segment 1103 may vary. For example, the number of wires used to form each transition segment may decrease as transition segment 1103 moves closer to distal segment 1105, to thereby provide gradual increase in flexibility from proximal segment 1102 to distal segment 1105.

Distal segment 1105 may be configured to be atraumatic, and thus, may be configured to be very flexible. Accordingly, distal segment 1105 may be more flexible than proximal segment 1102 and at least one transition segment 1103. In order to maintain flexibility, distal segment 1105 may be formed of about one to five wires. For example, distal segment 1105 may be formed of about one wire or two wires, and thus, may enable small coil winding, which may determine the flexibility of distal segment 1105.

While proximal segment 1102, transition segment 1103, and distal segment 1105 appear to have a constant cable diameter in FIG. 11A, the segments may not necessarily have a constant diameter. For example, the diameter of transition segment 1103 may be smaller than the diameter of proximal segment 1102, and the diameter of distal segment 1105 may be smaller than the diameter of the transition segment 1103. By way of example, the diameter of hollow shaft 1104 may gradually decrease from proximal segment 1102 to distal segment 1105. Accordingly, coil winding may decrease from proximal segment 1102 to distal segment 1105, to thereby achieve rigidity at proximal segment 1102, relative to distal segment 1105, and flexibility at distal segment 1105, relative to proximal segment 1102. Rigidity may gradually decrease from proximal segment 1102 to distal segment 1105.

Figure 11B:
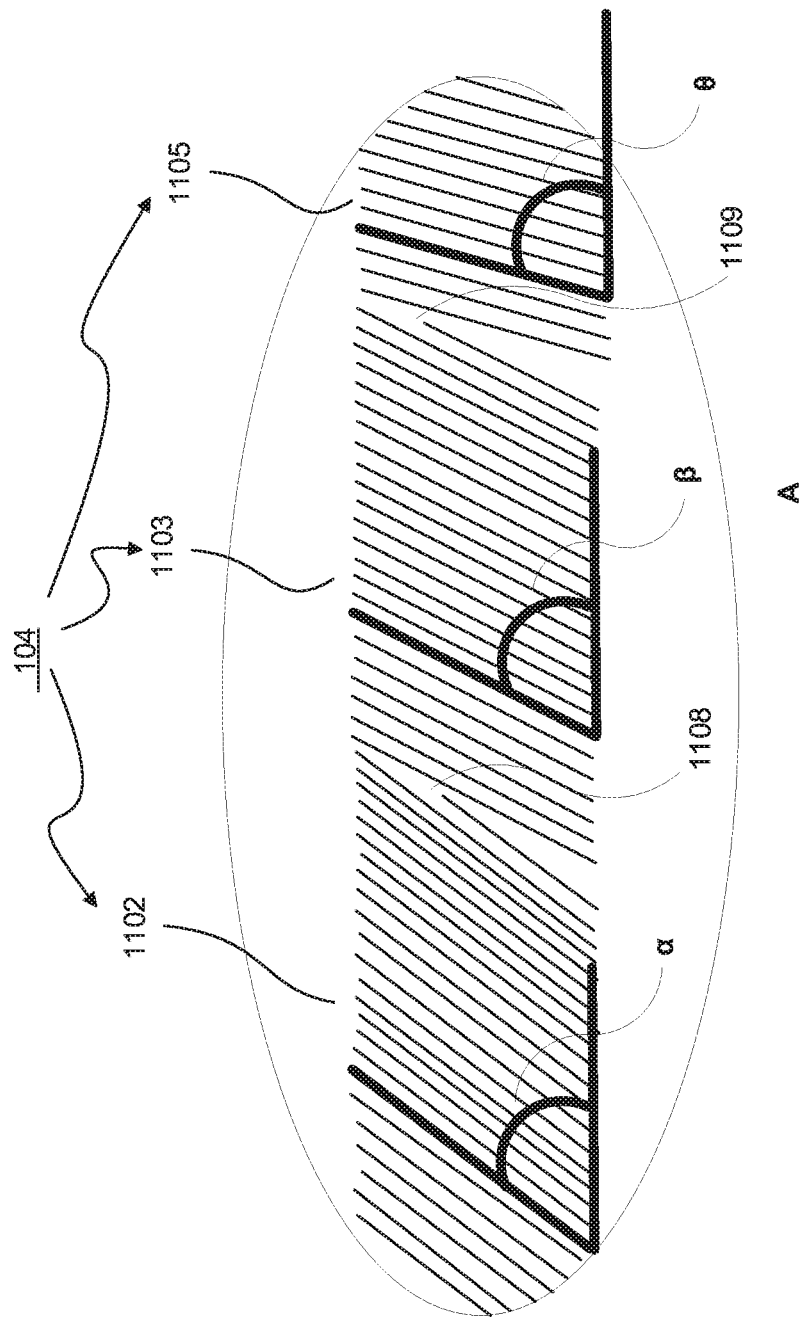
FIG. 11B illustrates a section of the exemplary endovascular device of FIG. 11A, consistent with various embodiments of the present disclosure.

FIG. 11B illustrates section A of exemplary endovascular device 1101 of FIG. 11A, in accordance with the disclosure.

In addition to decreasing the number of wires, the pitch angle at which the wires are wound may vary from proximal segment 1102 to distal segment 1105, to thereby transfer maximum torque while maintaining tip flexibility and structural strength of endovascular device 1101. As seen in FIG. 11B, proximal segment 1102 may be formed of a first number of wires wound at a first pitch angle $\alpha$. In addition, at least one transition segment 1103 may be formed of a second number of wires (less than the first number of wires) wound at a second pitch angle $\beta$. Finally, distal segment 1105 may be formed of a third number of wires (less than the second number of wires) wound at a third pitch angle $\theta$. As illustrated in FIG. 11B, the pitch angle may refer to the angle, relative to the bottom planar surface of the hollow shaft 1104, at which the wires are wound. The pitch angle, at which the wires are wound to form the cable, may increase gradually from proximal segment 1102 to distal segment 1105. For example, pitch angle $\alpha$ may be smaller than pitch angle $\beta$, and pitch angle $\beta$ may be smaller than pitch angle $\theta$. Increasing the pitch angle $\theta$ at distal segment 1105 may make distal segment 1105 more bendable. Although FIG. 11B only illustrates one transition segment 1103 formed of wires wound at pitch angle $\beta$, hollow shaft 1104 may include two or more transition segments 1103 at varying pitch angles. For example, hollow shaft 1104 may include a first transition segment and a second transition segment, and the first transition segment may be formed of wires wound at a smaller pitch angle than the wires forming the second transition segment. In some embodiments, hollow shaft 1104 may include at least three transition segments 1103.

In some embodiments, the pitch angle may be determined by various parameters, including, for example, a diameter of a winding mandrel, a diameter of the wire, and a number of wires required to form each segment. By way of example, assuming that the diameter of the wire and the initial cable diameter are known, then the diameter of the winding mandrel and the number of wires required may be calculated to obtain the optimal pitch angle. As such, the diameter of the winding mandrel may be increased or decreased to compensate for any changes in the pitch angle.

In order to provide a gradual transition in flexibility by decreasing the number of wires used from proximal segment 1102 and ultimately to distal segment 1105, the wires may need to be cut. By way of example, at a distal end 1108 of proximal segment 1102, one or more wires used to form proximal segment 1102 may be cut or removed during the winding process. Then, the remaining wires used to form proximal segment 1102 may be used to continue winding and forming transition segment 1103. Likewise, at a distal end 1109 of transition segment 1103, one or more wires used to form transition segment 1103 may be cut or removed during the winding process. Then, the remaining wires used to form proximal segment 1102 and transition segment 1103 may be used to continue winding and forming distal segment 1105. If hollow shaft 1104 includes two or more transition segments 1103, the process may be repeated by removing more wires and continuing to wind the remaining wires to form another transition segment 1103. As such, at least one common wire may be continuously wound to form proximal segment 1102, at least one transition segment 1103, and distal segment 1105. Therefore, instead of forming separate segments and connecting the segments together, the entire cable with proximal segment 1102, at least one transition segment 1103, and distal segment 1105 can be made with the same wire. By providing a continuous, gradual cable without any connection points along the cable, this obviates the need to incorporate rigid connections to connect separate segments together, thereby improving the flexibility of the cable.

Figure 11C:
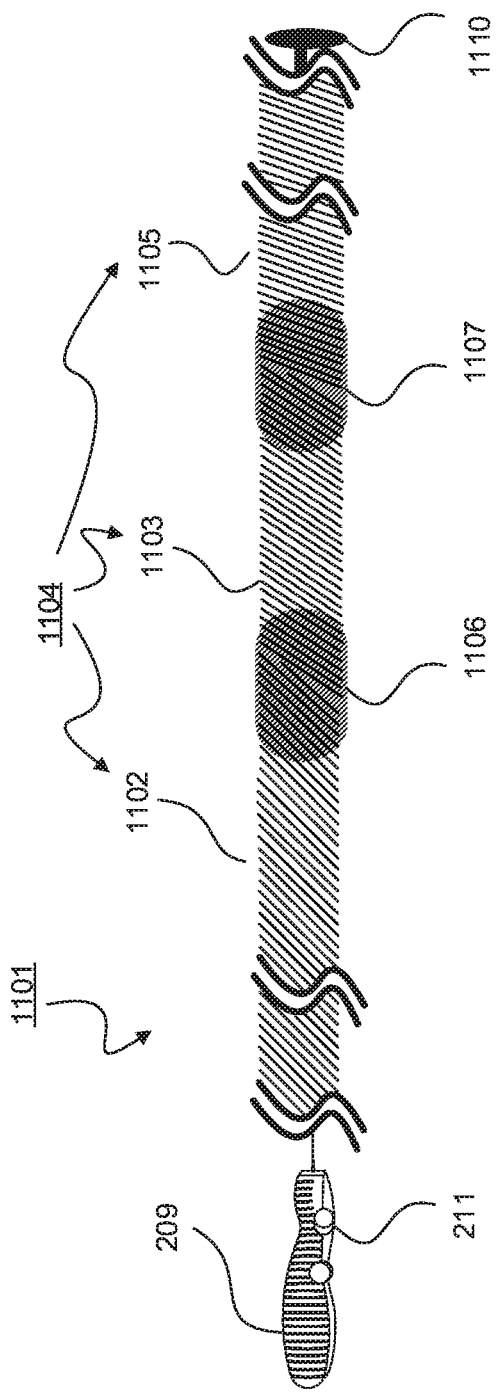
FIG. 11C illustrates the exemplary endovascular device of FIG. 11A, consistent with various embodiments of the present disclosure.

Once wires are cut during the winding process, exposed edges of the cut wires may be dangerous, particularly when endovascular device 1102 needs to be inserted inside the blood vessel. Therefore, as seen in FIG. 11C, once the winding process is finished, the cable may be post-processed by cutting any excess wires and covering the exposed edges of the cut wires with a material 1106. By way of example, material 1106 used to cover exposed edges of the cut wires may include any adhesives, epoxy glues, heat shrink, polyether ether ketone (PEEK), or any other bonding material.

In some embodiments, after wires are cut or removed during the winding process, the pitch angle at which the wires are wound may also change as a result, and thereby reduce the optimal torque transmission of the cable. Accordingly, a diameter of the winding mandrel may need to be adjusted in order to compensate for the wire removal. By way of example, at the distal end 1108 of proximal segment 1102 or at the distal end 1109 of transition segment 1103, one or more wires may be cut or removed. Therefore, at the distal end 1108 of proximal segment 1102 or at the distal end 1109 of transition segment 1103, the diameter of the winding mandrel may be decreased in order to compensate for the reduction in the number of wires used to form each segment. By decreasing the diameter of the winding mandrel, the pitch angle, at which the wires are wound to form each segment, may remain optimal without any overlapping of wires. For example, by decreasing the diameter of the winding mandrel, the pitch angle may remain constant without any overlapping of the wires. The diameter of the winding mandrel may be determined based on the number of wires used, the diameter of the wires, and the required pitch angle at each segment.

Figure 12A:
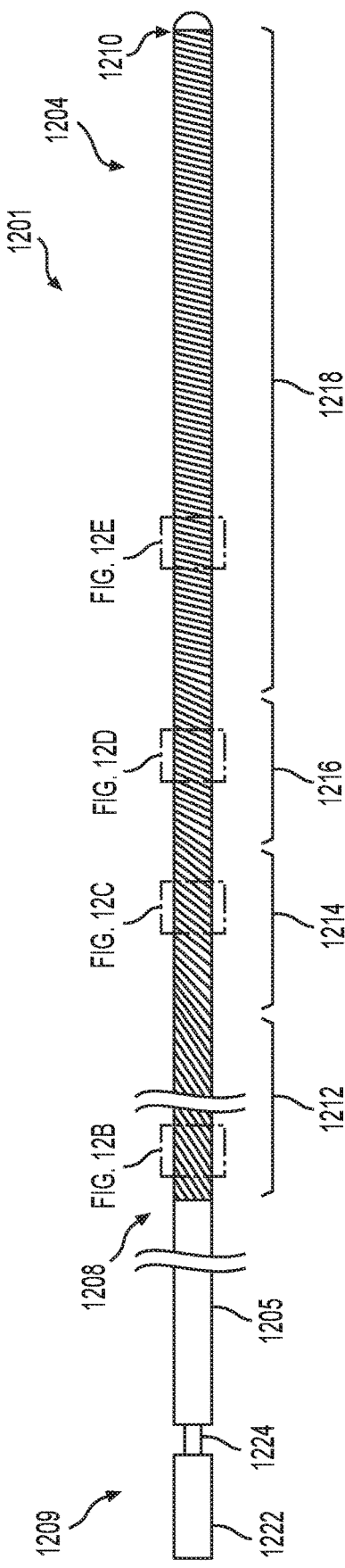
FIG. 12A illustrates an exemplary endovascular device, consistent with various embodiments of the present disclosure.

FIG. 12A illustrates an exemplary endovascular device 1201 in a straightened configuration, according to various embodiments of the present disclosure. Endovascular device 1201 may include an elongated sheath 1205 (e.g., tube 205 as depicted in FIG. 2 or tube 705 as depicted in FIG. 7) and an elongated coil 1204 connected to the distal end of sheath 1205. Coil 1204 may have a proximal end 1208 and a distal end 1210 and may be formed from a plurality of wires that are wound in a helical arrangement to form a hollow coil having at least one channel extending therethrough. Some or all of the wires of coil 1204 may extend to the coil distal end 1210, which may form the distal tip of endovascular device 1201. The wires of coil 1204 may, for example, be made from Nitinol with an outer diameter of approximately 75 µm. In some embodiments, coil 1204 may have an axial length of between approximately 400 and 500 mm. For example, coil 1204 may have an axial length of between approximately 430 mm and 440 mm.

In some embodiments, sheath 1205 may be a hollow, cylindrical hypotube constructed of an alloy or metal (e.g., nickel-titanium alloy, or Nitinol), stainless steel, a polymer, a synthetic material (e.g., nylon, polyether block amide (PEBA), or PEEK), and/or another suitable material. In some embodiments, sheath 1205 may have an outer diameter of between approximately 0.35 mm and 0.40 mm. For example, sheath 1205 may have an outer diameter of 0.35 mm, 0.36 mm, 0.37 mm, 0.38 mm, 0.39 mm, or 0.40 mm. In some embodiments, sheath 1205 may have an inner diameter of between approximately 0.20 mm and 0.25 mm. In some embodiments, sheath 1205 may have an axial length of between approximately 130 cm and 150 cm. For example, sheath 1205 may have an axial length of approximately 140 cm, 141 cm, or 142 cm. In some embodiments, material composition of sheath 1205 may vary towards the distal end of sheath 1205. For example, a proximal portion of sheath 1205 may be constructed from a kink-resistant material (e.g., Nitinol) and a distal portion of sheath 1205 may be constructed from a more rigid material (e.g., stainless steel) for improved pushability and to enhance torque transmission from the proximal end of sheath 1205 to coil 1204.

Figure 12E:
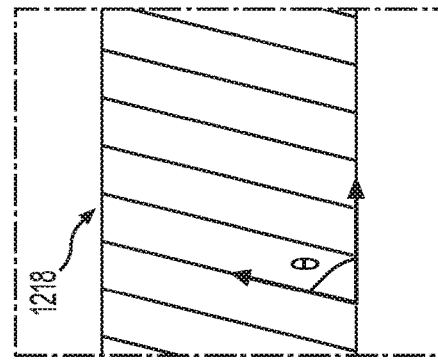
FIGS. 12B-12E illustrate enlarged views of different segments of the exemplary endovascular device of FIG. 12A, consistent with various embodiments of the present disclosure.
Figure 12D:
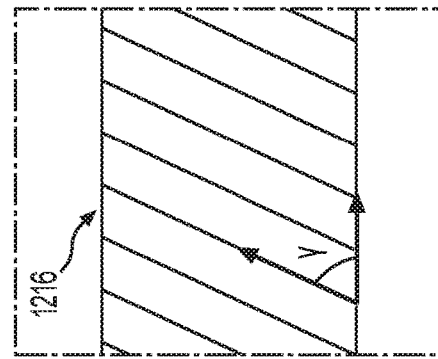
Figure 12C:
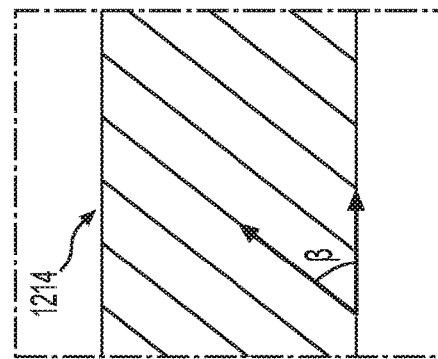

Endovascular device 1201 may also include a handle 1209 connected to the proximal end of sheath 1205 that may be actuated by a user to control movement of coil 1204, including bending and straightening of coil 1204. In some embodiments, handle 1209 may have a similar configuration as handle 209 depicted in FIG. 2 and may include a slider connected to a control wire (i.e., a core wire) extending through sheath 1205 and coil 1204 (not pictured in FIG. 12A). In some alternative embodiments, handle 1209 may include a user actuation segment 1222 at its proximal end that is configured for movement relative to sheath 1205. A core wire (not pictured in FIG. 12A) may be connected to user actuation segment 1222 and to coil distal end 1210. As illustrated in FIG. 12F, movement (e.g., axial movement) of user actuation segment 1222 relative to sheath 1205 may cause the core wire to exert a force on coil distal end 1210, causing straightening or bending of coil 1204. In some embodiments, user actuation segment 1222 may be cylindrical, with an outer diameter substantially equal to the outer diameter of sheath 1205. User actuation segment 1222 may be at least partially hollow and may be constructed of an alloy or metal (e.g., nickel-titanium alloy), stainless steel, a polymer, and/or another suitable material. Although handle 1209 is depicted as including a user actuation segment 1222 in FIG. 12A, one of ordinary skill will understand that the handle of exemplary endovascular device 1201 may include any suitable mechanism for controlling bending and straightening of elongated coil 1204, such as a wheel, a slider, a lever, a joystick, a touchpad, a rotatable cuff, or any other structure configured to control bending and straightening of coil 1204.

In some embodiments, handle 1209 may also include an inner member 1224 situated at least partially within user actuation segment 1222 and at least partially within sheath 1205, with the core wire extending through inner member 1224. In some embodiments, inner member 1224 may be connected to user actuation segment 1222 or to sheath 1205 in order to guide and support the movement of user actuation segment 1222 relative to sheath 1205. In some embodiments, inner member 1224 may be configured as the locking inner member disclosed in WO 2019/116102 A2, which is incorporated herein by reference in its entirety.

Coil 1204 may be formed from a plurality of wires and may include a proximal coil segment 1212, a first transition segment 1214, a second transition segment 1216, and a distal coil segment 1218. In some embodiments, proximal coil segment 1212 may include coil proximal end 1208 and may be configured to be more rigid than the other segments of coil 1204, such that proximal coil segment 1212 may be configured to transfer torque to the rest of coil 1204. Proximal coil segment 1212 may be formed of a first number of wires, and the first number of wires required to form proximal coil segment 1212 may be based on certain constraints. For example, certain constraints may include an outer diameter of the coil, an inner diameter of the coil, or an optimal coil angle for torque transfer. In some embodiments, proximal coil segment 1212 may be formed of about six to 16 wires that are helically wound to form a coil. For example, proximal coil segment 1212 may be formed of ten wires that are helically wound and that extend along the entire axial length of proximal coil segment 1212. In some embodiments, proximal coil segment 1212 may have an axial length of between approximately 400 mm and 425 mm. For example, proximal coil segment 1212 may have an axial length of approximately 410 mm.

Figure 12B:
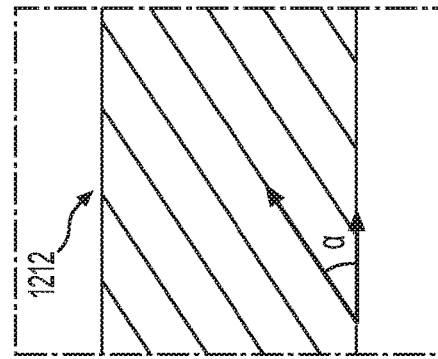
Figure 12F:
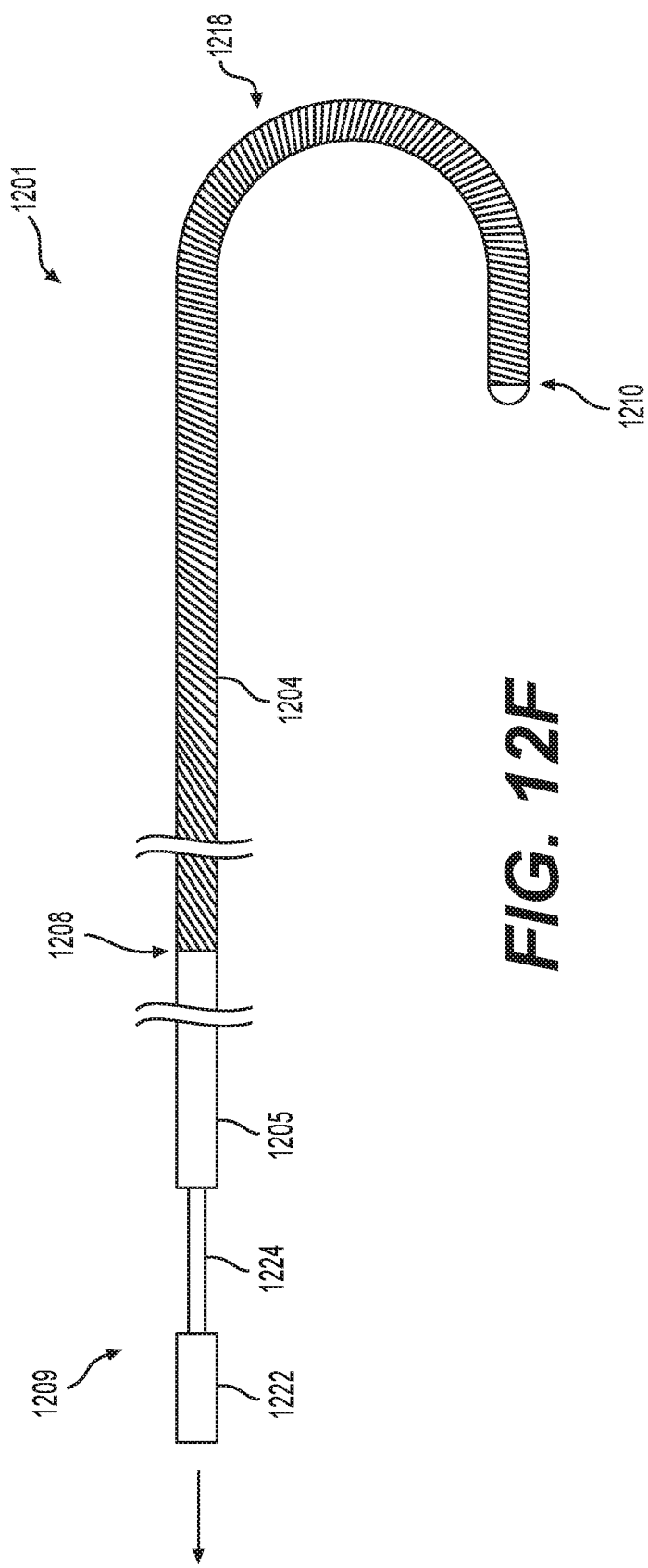
FIG. 12F illustrates the exemplary endovascular device of FIG. 12A in a curved configuration, consistent with various embodiments of the present disclosure.

FIG. 12B illustrates an enlarged view of proximal coil segment 1212. As shown, the wires of proximal coil segment 1212 may be wound at a first coil angle α, relative to the bottom planar surface of coil 1204 and, thus, to the longitudinal axis of coil 1204. In some embodiments, first coil angle α may be an angle of between 55° and 65°. In some embodiments, the number of wires used to form proximal coil segment 1212 may be selected based at least in part on the wire diameter and the diameter of a mandrel upon which proximal coil segment 1212 is formed, so as to achieve the desired first coil angle α. For example, ten wires with outer diameters of 75 μm may be braided on a mandrel with an outer diameter of approximately 0.36 mm to form a proximal coil segment 1212 having the desired first coil angle α of approximately 57°. As another example, nine wires with outer diameters of 85 μm may be braided on a mandrel with an outer diameter of approximately 0.36 mm to form a proximal coil segment 1212 having the desired first coil angle α of approximately 56°.

Referring again to FIG. 12A, elongated coil 1204 may additionally include at least two transition segments 1214 and 1216 adjacent to proximal coil segment 1212. Transition segments 1214 and 1216 may be configured to provide a gradual increase in flexibility between proximal coil segment 1212 and a distal coil segment 1218. In the embodiment illustrated in FIG. 12A, coil 1204 may include two transition segments 1214 and 1216. In some alternative embodiments, coil 1204 may include three transition segments, four transition segments, five transition segments, six transition segments, or any other suitable number of transition segments. The number of transition segments may vary based on various parameters, including rigidity of proximal coil segment 1212, flexibility of distal coil segment 1218, the axial length of elongated coil 1204, or the number of wires used to form coil 1204.

First transition segment 1214 may be immediately adjacent to proximal coil segment 1212 and may be formed from fewer wires than proximal coil segment 1212, such that first transition segment 1214 may be configured for greater flexibility than proximal coil segment 1212. In some embodiments, first transition segment 1214 may be formed from four to nine wires. For example, first transition segment 1214 may be formed of six wires that are helically wound and that extend along the entire axial length of first transition segment 1214. In some embodiments, first transition segment 1214 may have an axial length of between approximately 3.0 mm and 8.0 mm. For example, first transition segment 1214 may have an axial length of approximately 5.0 mm.

FIG. 12C illustrates an enlarged view of first transition segment 1214. As shown, the wires of first transition segment 1214 may be wound at a second coil angle β, relative to the bottom planar surface of coil 1204 and, thus, to the longitudinal axis of coil 1204. In some embodiments, second coil angle β may be an angle of between 55° and 65° and may be larger than the first coil angle α. In some embodiments, the number of wires used to form first transition segment 1214 may be selected based at least in part on the wire diameter and the diameter of a mandrel upon which first transition segment 1214 is formed, so as to achieve desired second coil angle β. For example, six wires with outer diameters of 75 μm may be braided on a mandrel with an outer diameter of approximately 210 μm to form a first transition segment 1214 having the desired second coil angle β of approximately 60°.

Referring again to FIG. 12A, second transition segment 1216 may be immediately adjacent to first transition segment 1214 and may be formed from fewer wires than first transition segment 1214, such that second transition segment 1216 may be configured for greater flexibility than first transition segment 1214. In some embodiments, second transition segment 1216 may be formed from three to eight wires. For example, second transition segment 1216 may be formed of four wires that are helically wound and that extend along the entire axial length of second transition segment 1216. In some embodiments, second transition segment 1216 may have an axial length of between approximately 3.0 mm and 8.0 mm. For example, second transition segment 1216 may have an axial length of approximately 5.0 mm. In some embodiments, first transition segment 1214 and second transition segment 1216 may have the same axial length.

FIG. 12D illustrates an enlarged view of second transition segment 1216. As shown, the wires of second transition segment 1216 may be wound at a third coil angle γ, relative to the bottom planar surface of coil 1204 and, thus, to the longitudinal axis of coil 1204. In some embodiments, third coil angle γ may be an angle of between 65° and 75° and may be larger than the second coil angle β. In some embodiments, the number of wires used to form second transition segment 1216 may be selected based at least in part on the wire diameter and the diameter of a mandrel upon which second transition segment 1216 is formed, so as to achieve desired third coil angle γ. For example, four wires with outer diameters of 75 μm may be braided on a mandrel with an outer diameter of approximately 210 μm to form a second transition segment 1216 having the desired third coil angle γ of approximately 70°.

Referring against to FIG. 12A, distal coil segment 1218 may be immediately adjacent to second transition segment 1216 and may include coil distal end 1210. Distal coil segment 1218 may be configured to be very flexible such that distal coil segment 1218 may be atraumatic as endovascular device 1201 is advanced through the body. In some embodiments, distal coil segment 1218 may be more flexible than the other segments of coil 1204, including second transition segment 1216. Distal coil segment 1218 may be formed of about one to four wires. For example, distal coil segment 1218 may be formed of one wire or of two wires that are helically wound into a coil. Advantageously, forming distal coil segment 1218 from two wires may provide a soft and atraumatic distal coil segment 1218, while still maintaining the ability of distal coil segment 1218 to transmit torque applied to the proximal end of endovascular device 1201. In some embodiments, distal coil segment 1218 may have an axial length of between approximately 15 mm and 25 mm. For example, distal coil segment 1218 may have an axial length of approximately 20 mm. Due to the decreasing number of wires between the different segments of coil 1204, the flexibility of coil 1204 may gradually increase in a longitudinal direction from coil proximal end 1208 to coil distal end 1210. Advantageously, the decreasing number of wires in coil 1204 may achieve rigidity at proximal coil segment 1212, relative to distal coil segment 1218, and flexibility at distal coil segment 1218, relative to proximal coil segment 1212. In addition, rigidity may gradually decrease in the longitudinal direction from proximal coil segment 1212 to distal coil segment 1218. Accordingly, endovascular device 1201 may be easily maneuvered through narrow, tortuous body lumens (such as intracranial vessels) because of the torqueability provided by proximal coil segment 1212 to the rest of elongated coil 1204, while avoiding injury to the surrounding anatomy because of the flexible, atraumatic distal coil segment 1218 forming the tip of the endovascular device.

FIG. 12E illustrates an enlarged view of distal coil segment 1218. As shown, the wires of distal coil segment 1218 may be wound at a fourth coil angle θ, relative to the bottom planar surface of coil 1204 and, thus, to the longitudinal axis of coil 1204. In some embodiments, fourth coil angle θ may be an angle of between 77° and 83° and may be larger than the third coil angle γ. In some embodiments, the number of wires used to form distal coil segment 1218 may be selected based at least in part on the wire diameter and the diameter of a mandrel upon which distal coil segment 1218 is formed, so as to achieve desired fourth coil angle θ. For example, two wires with outer diameters of 75 μm may be braided on a mandrel with an outer diameter of approximately 210 μm to form a distal coil segment 1218 having the desired fourth coil angle θ of approximately 80°.

In addition to decreasing the number of wires along coil 1204, the coil angle at which the wires are wound may vary from proximal coil segment 1212 to distal coil segment 1218. The variation in coil angle may allow the transfer of maximum torque from proximal coil segment 1212 to the rest of coil 1204, while also maintaining the desired flexibility of distal coil segment 1218 and the structural strength of the entire endovascular device 1201. In some embodiments, the coil angle at which the wires are wound to form coil 1204 may increase gradually from proximal coil segment 1212 to distal coil segment 1218. For example, second coil angle β may be larger than the coil angle α. Additionally, or alternatively, third coil angle γ may be larger than second coil angle β. Additionally, or alternatively, fourth coil angle θ may be larger than third coil angle γ. Advantageously, an increase in the coil angle may increase the flexibility of the corresponding section of coil 1204; thus, distal coil segment 1218 may have the largest coil angle and may accordingly be the most flexible segment of coil 1204. Similarly, proximal coil segment 1212 may have the smallest coil angle and may accordingly be the most rigid segment of coil 1204.

In the embodiment illustrated in FIG. 12A, coil 1204 may have a constant diameter along its entire axial length. For example, proximal coil segment 1212, first transition segment 1214, second transition segment 1216, and distal coil segment 1218 may have a constant outer diameter of between approximately 0.35 mm and 0.40 mm, for example, an outer diameter of 0.35 mm, 0.36 mm, 0.37 mm, 0.38 mm, 0.39 mm, or 0.40 mm. In some alternative embodiments, the diameter of coil 1204 may gradually decrease from proximal coil segment 1212 to distal coil segment 1218. For example, proximal coil segment 1212 may have an outer diameter of between approximately 0.35 mm and 0.40 mm, and distal coil segment 1218 may have an outer diameter of between approximately 0.32 mm and 0.38 mm. Advantageously, the reduced diameter of distal coil segment 1218 may enable the distal coil segment to have a desired flexibility that is greater than the flexibility of proximal coil segment 1212. In some embodiments, proximal coil segment 1212, first transition segment 1214, second transition segment 1216, and distal coil segment 1218 may be aligned axially along coil 1204 to form a single, unitary structure with a flexibility that gradually increases from coil proximal end 1208 to coil distal end 1210.

FIG. 12F illustrates an exemplary configuration of endovascular device 1201 in which at least a portion of coil 1204 is bent into a curved configuration, according to various embodiments of the present disclosure. In some embodiments, some or all of distal coil segment 1218 may be configured to bend into the curved configuration. In some embodiments, a core wire (not shown in FIG. 12F) may extend between a portion of handle 1209 (e.g., user actuation segment 1222) and a portion of coil 1204 at or near coil distal end 1210. As shown in FIG. 12F, axial movement of the core wire (e.g., due to movement of user actuation segment 1222 relative to sheath 1205) may radially bend coil 1204, including distal end 1210, from a straight configuration (e.g., the configuration illustrated in FIG. 12A) into a curved or angled configuration, or from a curved or angled configuration to a straight configuration or into a different curved or angled configuration. In some embodiments, the bending portion of coil 1204 may be configured to bend in a single direction from the straight configuration (e.g., from a straight configuration towards a left-hand side, but not towards a right-hand side) due to the actuation of handle 1209. In other embodiments, the bending portion of coil 1204 may be configured to bend in two opposite directions from the straight configuration (e.g., both to the left-hand side and the right-hand side from the straight configuration) due to the actuation of handle 1209.

Figure 13A:
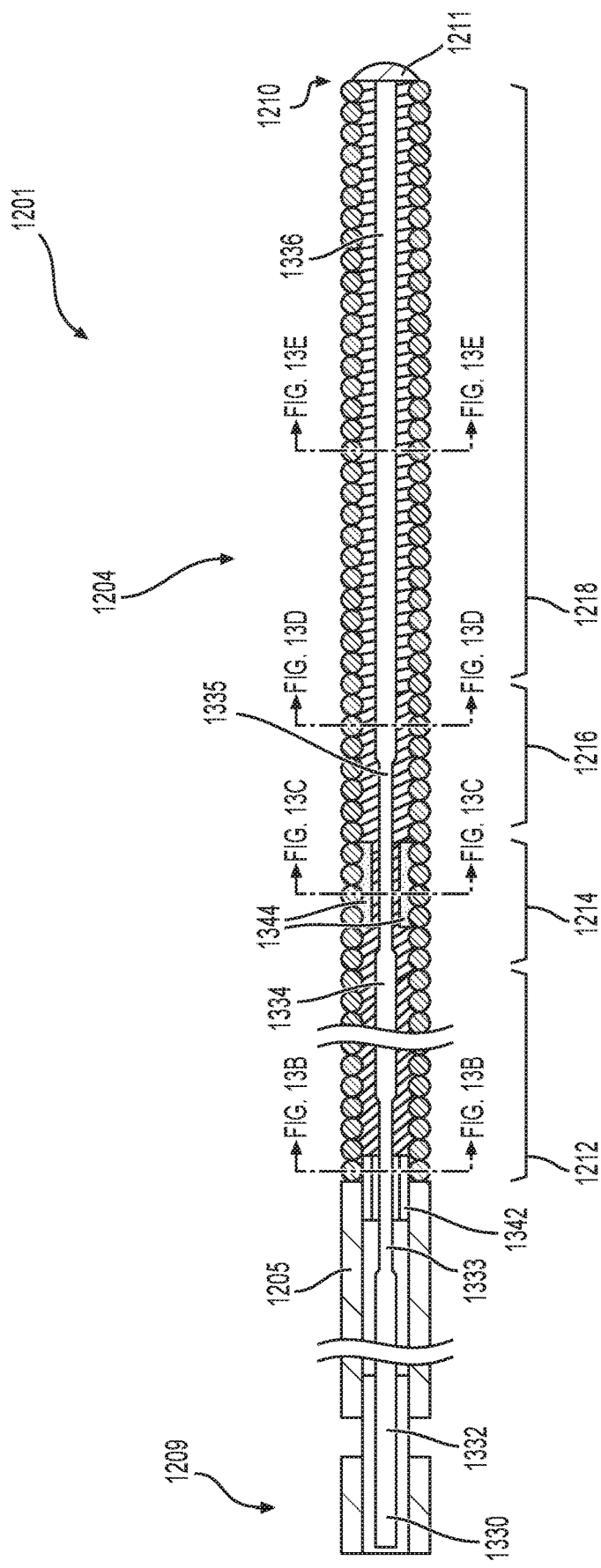
FIG. 13A illustrates an interior view of the exemplary endovascular device of FIG. 12A, consistent with various embodiments of the present disclosure.

FIG. 13A illustrates an interior view of endovascular device 1201, in accordance with various embodiments of the present disclosure. Endovascular device 1201 may include at least one core wire 1330 extending between handle 1209 and coil distal end 1210 to control bending and straightening of coil 1204. In the embodiment depicted in FIG. 13A, the distal end of core wire 1330 may be connected to coil distal end 1210 via a dome cap 1211, which may be constructed of epoxy and may be rounded to prevent injury to tissue.

Core wire 1330 may be constructed of an alloy or metal (e.g., nickel-titanium alloy, or Nitinol), stainless steel, a polymer, and/or another suitable material, and may have a polytetrafluoroethylene (PTFE) coating. In some embodiments, core wire 1330 may include zones having different cross-sectional shapes and/or dimensions. For example, core wire 1330 may include core wire zones 1332, 1334, and 1336 with circular cross-sections and two or more core wire zones 1333 and 1335 in which the cross-sectional area of core wire 1330 is reduced, relative to core wire zones 1332, 1334, and 1336. In some embodiments, core wire zones 1332, 1334, and 1336 may have circular cross-sections with outer diameters of between approximately 0.12 mm and 0.18 mm. For example, core wire zones 1332, 1334, and 1336 may have an outer diameter of approximately 0.15 mm.

In some embodiments, core wire 1330 may have a similar configuration as control wire 101 as depicted in FIG. 1. For example, core wire zones 1333 and 1335 may have cross-sections that are non-circular (e.g., elliptical, oval-shaped, rectangular, etc.) and may have smaller cross-sectional areas than core wire zones 1332, 1334, and 1336. For example, in some embodiments core wire zones 1333 and 1335 may be formed by selectively flattening or otherwise deforming portions of core wire 1330. In some alternative embodiments, the non-circular core wire zones 1333 and 1335 may be formed by adhesion of additional materials to portions of core wire 1330 to form a non-round shape. In some alternative embodiments, core wire 1330 as depicted in FIG. 13A may have a similar configuration as control wire 601 as depicted in FIG. 6. For example, core wire 1330 may include one core wire zone having a non-circular cross-section. In some further alternative embodiments, core wire 1330 may include zero core wire zones, three core wire zones, four core wire zones, or any other suitable number of core wire zones having non-circular cross-sections. In some embodiments, core wire zone 1333 may have an axial length of between approximately 30 mm and 45 mm (e.g., an axial length of approximately 40 mm). Additionally, or alternatively, core wire zone 1335 may have an axial length of between approximately 20 mm and 30 mm (e.g., an axial length of approximately 26 mm). In some embodiments, core wire zone 1335 may have a shorter axial length than core wire zone 1333, and approximately 400 mm of core wire 1330 may be provided between the distal end of core wire zone 1335 and the distal end of core wire zone 1333.

FIG. 13B illustrates a cross-sectional view of endovascular device 1201 at coil proximal end 1208, near the location at which sheath 1205 is connected to proximal coil segment 1212. A portion of core wire zone 1333 may extend through coil proximal end 1208. As shown in FIG. 13B, core wire zone 1333 may have a non-circular cross-section, with a first dimension of the core wire (pictured as the height in FIG. 13B) being smaller than a second, perpendicular dimension of the core wire (pictured as the width in FIG. 13B). Although core wire zone 1333 depicted in FIG. 13 has an oval-shaped cross-section, one of ordinary skill will understand that core wire zone 1333 may have any suitable non-circular cross-sectional shape in which the height of the core wire is smaller than the width of the core wire. In some embodiments, core wire zone 1333 may have a height of between approximately 0.10 mm and 0.15 mm. For example, core wire zone 1333 may have a height of approximately 0.12 mm. Additionally, or alternatively, core wire zone 1333 may have a width of approximately 0.15 mm.

As shown in FIG. 13B, proximal coil segment 1212 may include ten wires wound into a helical coil, with an opening in the center of proximal coil segment 1212 through which core wire 1330 may extend. Optionally, an anti-rotation mechanism may be provided at or near coil proximal end 1208 to prevent axial rotation between core wire 1330 and the shaft 1205 and coil 1204, without preventing relative axial movement between core wire 1330 and the shaft 1205 and coil 1204. In the embodiment of FIG. 13B, an internal connector 1342 may be provided at coil proximal end 1208, extending between the inner lumens of sheath 1205 and coil 1204. An adhesive or bonding material 1344 (e.g., PEEK) may be provided in the spaces between internal connector 1342 and sheath 1205 and/or in the spaces between internal connector 1342 and proximal coil segment 1212. Thus, internal connector 1342 may secure sheath 1205 and coil 1204 together.

Internal connector 1342 may be a hollow tube constructed of an alloy or metal (e.g., nickel-titanium alloy, or nitinol), stainless steel, a polymer, and/or another suitable material. In some embodiments, internal connector 1342 may have an axial length of between approximately 3.0 mm and 30 mm. For example, internal connector 1342 may have an axial length of between approximately 4.0 mm and 16 mm. In some embodiments, internal connector 1342 may have an outer diameter of approximately 0.20 mm and an inner diameter of approximately 0.16 mm. In some embodiments, internal connector 1342 may have an elliptical or oval-shaped cross-section (as shown in FIG. 13B) through which core wire zone 1333 of the core wire may extend. Internal connector 1342 and core wire zone 1333 may be similarly configured in that both features have a smaller first dimension (pictured as the height in FIG. 13B) and a larger second dimension (pictured as the width in FIG. 13B. In addition, the inner diameter of internal connector 1342 may be slightly larger than the outer diameter of core wire zone 1333, such that a small amount of clearance may be provided between the internal connector 1342 and core wire zone 1333. As a result, internal connector 1342 and core wire zone 1333 may resist relative axial rotation of core wire 1330 relative to sheath 1205 and coil 1204, while permitting axial movement of core wire 1330 relative to sheath 1205 and coil 1204. Alternatively, other non-symmetrical shapes (e.g., cross-sections) may be employed, consistent with the present disclosure to resist rotation and to permit torqueing.

Additionally, or alternatively, a different anti-rotation mechanism may be provided at or near coil proximal end 1208 to prevent axial rotation between core wire 1330 and the shaft 1205 and coil 1204. For example, one or more polymers similar to polymers 208 in FIGS. 4 and 5 may be inserted between core wire 1330 and sheath 1205 and/or proximal coil segment 1212. The insertion of the polymers may prevent relative axial rotation between core wire 1330 and the shaft 1205 and coil 1204, without preventing relative axial movement between core wire 1330 and the shaft 1205 and coil 1204. In some further alternative embodiments, one or both of the shaft 1205 and coil 1204 may have an elliptical or oval-shaped cross-section at proximal coil end 1208, similar to the configurations of cable 706 and coil 707 illustrated in FIGS. 9 and 10, respectively. This elliptical cross-sectional shape may resist axial rotation of core wire 1330 relative to the shaft 1205 and coil 1204, enabling torqueing of endovascular device 1201. Alternatively, other non-symmetrical shapes (e.g., cross-sections) may be employed, consistent with the present disclosure to resist rotation and to permit torqueing.

FIG. 13C illustrates a cross-sectional view of endovascular device 1201 along first transition segment 1214 of coil 1204. First transition segment 1214 may include six wires wound into a helical coil, with an opening in the center of first transition segment 1214 through which core wire 1330 may extend. In some embodiments, and as discussed below, an anti-rotation mechanism may be provided within first transition segment 1214, so as to prevent axial rotation of core wire 1330 relative to coil 1204 without preventing relative axial movement between core wire 1330 and coil 1204. In some alternative embodiments, first transition segment 1214 of the coil may be provided without an anti-rotation mechanism. In such embodiments, core wire 1330 may have a round cross-sectional shape within first transition segment 1214, similar to core wire zones 1332, 1334, and 1336.

In some embodiments, a polymer 1346 may be provided within first transition segment 1214 as an anti-rotation mechanism. For example, one or more polymers 1346, such as PEEK, may be inserted through coil 1204 to form a non-round cross-section of the inner lumen of first transition segment 1214. A core wire zone 1335 with a reduced cross-sectional area may extend along polymer 1346, thus forming an anti-rotation mechanism of first transition segment 1214. As shown in FIG. 13C, core wire 1330 may have an oval-shaped cross-section at core wire zone 1335; alternatively, core wire 1330 may have any suitable cross-sectional shape at core wire zone 1335, such as a rectangular cross-section. In some embodiments, core wire 1330 may have a height of between approximately 0.10 mm and 0.15 mm at core wire zone 1335. For example, core wire 1330 may have a height of approximately 0.12 mm at core wire zone 1335. Coil wire zone 1335 may have an axial length that is equal to or shorter than the axial length of coil wire zone 1333. In some embodiments, core wire zone 1335 may have an axial length of between approximately 20 mm and 30 mm (e.g., an axial length of approximately 26 mm).

FIG. 13D illustrates a cross-sectional view of endovascular device 1201 along second transition segment 1216 of the coil, and FIG. 13E illustrates a cross-sectional view of endovascular device 1201 along distal coil segment 1218. As shown, second transition segment 1216 may include four wires wound into a helical coil, with an opening in the center of second transition segment 1216 through which core wire 1330 may extend. Additionally, or alternatively, distal coil segment 1218 may include two wires wound into a helical coil, with an opening in the center of distal coil segment 1218 through which core wire 1330 may extend. In some embodiments, the distal-most portion of core wire 1330 (which may have an axial length of, e.g., between approximately 20 mm and 40 mm) may have an outer diameter that is smaller than 0.15 mm or, in some embodiments, smaller than 0.12 mm.

Figure 14:
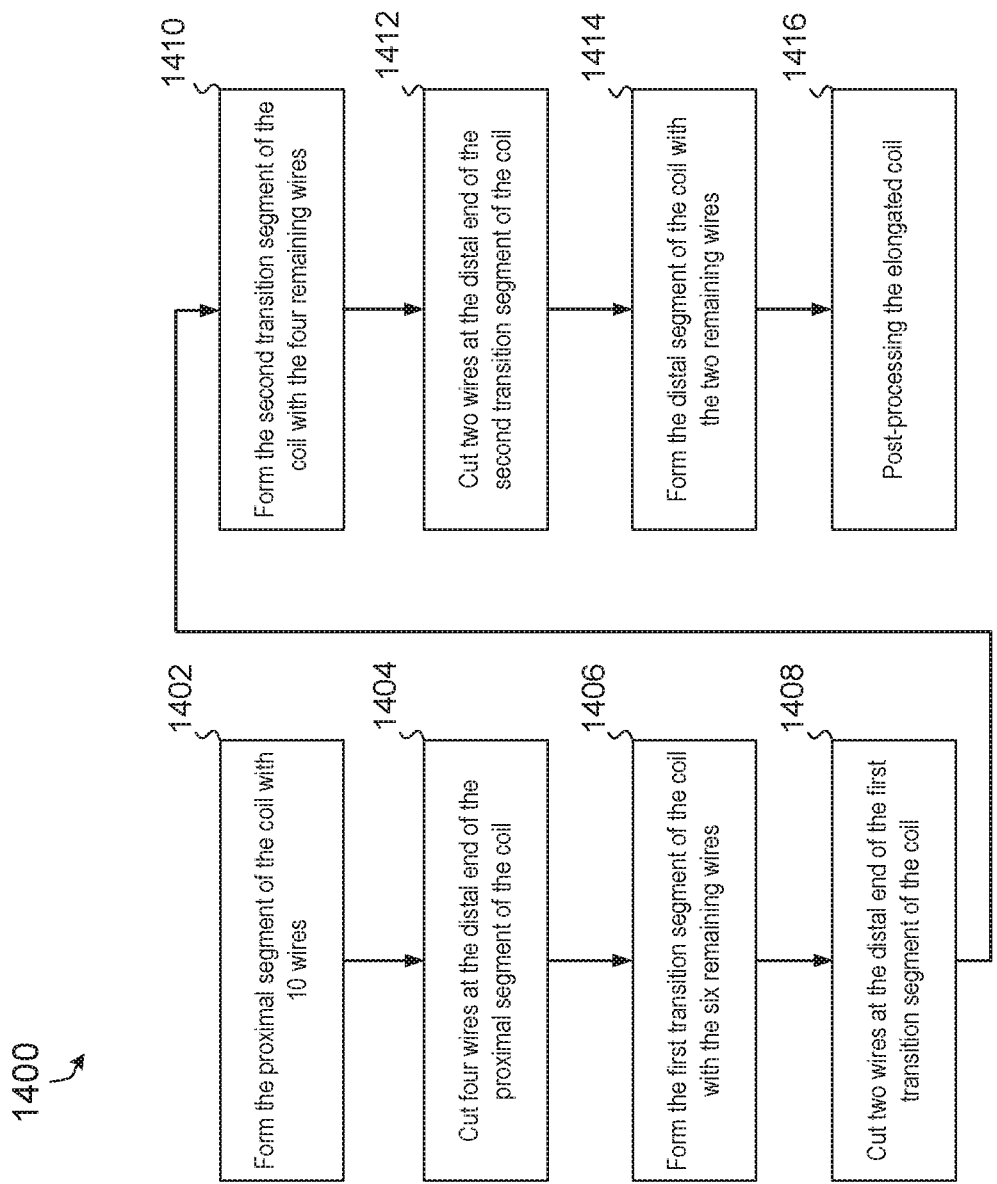
FIG. 14 illustrates an exemplary method of manufacturing an exemplary elongated coil of an endovascular device, consistent with various embodiments of the present disclosure.

FIG. 14 illustrates an exemplary method 1400 of manufacturing an elongated coil of an endovascular device. One of ordinary skill will understand that manufacturing method 1400 disclosed herein is merely exemplary and that other methods could be used to manufacture elongated coils of an endovascular device as disclosed herein. Moreover, exemplary method 1400 may be used to manufacture any suitable coil of an endovascular device, including and not limited to cable 206 (optionally, including coil 207), cable 706 (optionally, including coil 707), elongated shaft 1104, or elongated coil 1204. Although exemplary method 1400 as disclosed herein describes the manufacturing of an elongated coil with a proximal coil segment, a distal coil segment, and two transition segments between the proximal and distal coil segments, one of ordinary skill will understand that an elongated coil with any suitable number of transition segments may be manufactured according to method 1400, with at least one parameter of the elongated coil (e.g., number of wires, wire material(s), wire gauge, coil diameter, spacing between individual wires, and/or spacing between groups of wires) differing between each segment. For example, an exemplary coil manufactured according to method 1400 may include one transition segment, three transition segments, four transition segments, five transition segments, six transition segments, seven transition segments, eight transition segments, or any other suitable number of transition segments between the proximal and distal coil segments of the coil.

In step 1402 of method 1400, beginning from the proximal end of the elongated coil, between six wires and 16 wires (e.g., ten wires) may be helically wound towards the distal end of the elongated coil to form a proximal coil segment of the elongated coil. The ten wires may be continuously wound so as to form the proximal coil segment of the elongated coil as a single unitary structure. In some embodiments, the wires may be wound on a mandrel having a shape, dimensions, and configuration selected to produce a desired shape and size of the elongated coil. In step 1404 of method 1400, upon forming the distal end of the proximal coil segment of the elongated coil, a predetermined number (e.g., four) of the wires in the proximal coil segment may be cut or otherwise removed. In step 1406 of method 1400, the first transition segment of the coil may be formed by continuously winding the remaining wires towards the distal end of the elongated coil. The first transition segment may include between four wires and nine wires (e.g., six wires). In some embodiments, the six wires may be wound along a corresponding section of the mandrel. In step 1408 of method 1400, upon forming the distal end of the first transition segment, a predetermined number (e.g., two) of the wires in the first transition segment may be cut or otherwise removed. In step 1410 of method 1400, the second transition segment of the coil may be formed by continuously winding the remaining wires towards the distal end of the elongated coil. The second transition segment may include between three wires and eight wires (e.g., four wires). In some embodiments, the four wires may be wound along a corresponding section of the mandrel. In step 1412 of method 1400, upon forming the distal end of the second transition segment, a predetermined number (e.g., two) of the wires in the second transition segment may be cut or otherwise removed. In step 1414 of method 1400, the remaining wires may be continuously wound to form the distal coil segment of the elongated coil. The distal coil segment may include between one wire and four wires (e.g., two wires). In optional step 1416 of method 1400, after the wires are cut during the manufacturing method 1400, the elongated coil may be post-processed by cutting any excess wires and/or by covering exposed edges of the cut wires with a protective material, such as material 1106.

Advantageously, by cutting or otherwise removing wires from the elongated coil in steps 1404, 1408, and 1414, a gradual increase in flexibility may be formed from the proximal end of the elongated coil to the distal end of the elongated coil. In addition, forming the elongated coil by gradually removing wires between coil segments may allow the entire coil to be formed as a single, unitary structure and obviate the need to incorporate rigid connections to connect separate segments together, thereby improving the flexibility of the coil.

Figure 15:
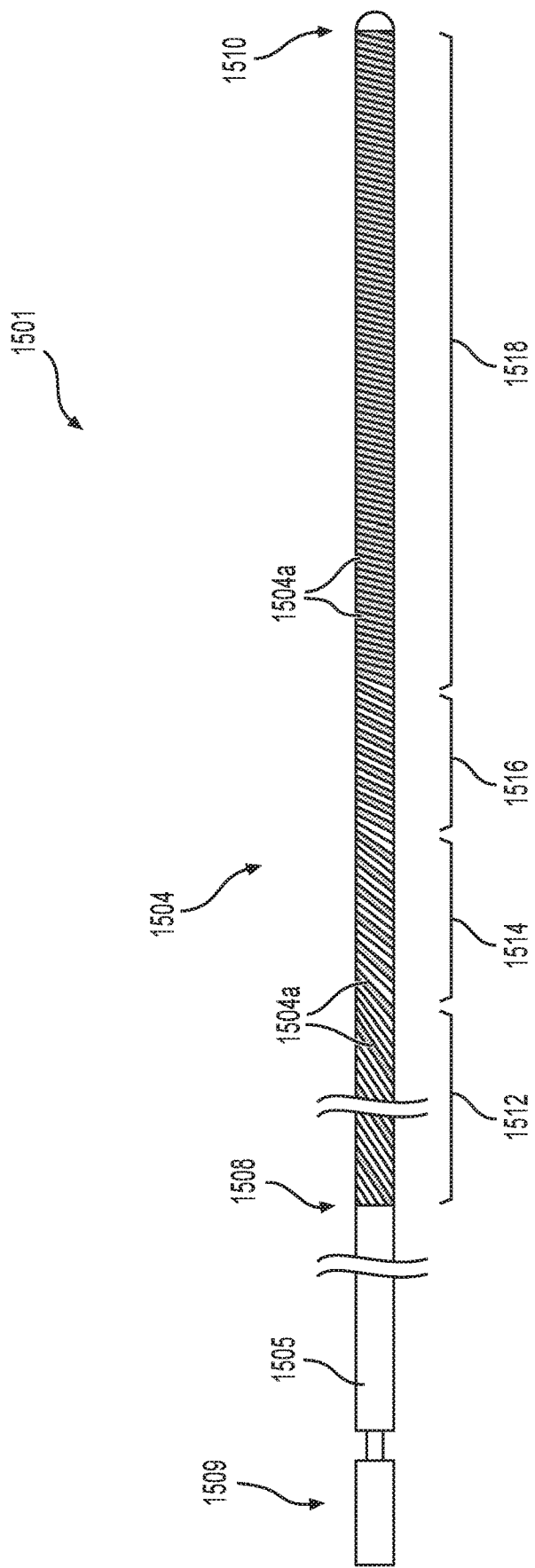
FIG. 15 illustrates an exemplary endovascular device, consistent with various embodiments of the present disclosure.

FIG. 15 illustrates an exemplary endovascular device 1501, according to various embodiments of the present disclosure. Endovascular device 1501 may include an elongated coil 1504, an elongated sheath 1505 connected to the proximal end of coil 1504, and a handle 1509 connected to the proximal end of sheath 1505. Coil 1504 may be formed from a plurality of helically-wound wires and may have a similar configuration as elongated coil 1204 as depicted in FIG. 12A: coil 1504 may include a proximal coil segment 1512, a first transition segment 1514, a second transition segment 1516, and a distal coil segment 1518. Proximal coil segment 1512 may be formed from between five and 12 nitinol wires (e.g., eight nitinol wires) and between one wire and four wires (e.g., two wires 1504*a*) that are formed of nitinol with radiopaque cores (e.g., 30% tantalum cores). These wires may be helically-wound to form proximal coil segment 1512, with a predetermined number (e.g., four) of the nitinol wires being cut at the distal end of proximal coil segment 1512. The remaining wires (for example, between three and five nitinol wires and between one and four nitinol wires with radiopaque cores) may be helically wound to form first transition segment 1514, with at least one additional nitinol wire (for example, another two nitinol wires) being cut at the distal end of first transition segment 1514. The remaining wires (for example, between two and four nitinol wires and between one and four nitinol wires with radiopaque cores) may be helically wound to form second transition segment 1516, with the remaining nitinol wires without radiopaque cores being cut at the distal end of second transition segment 1516. Distal coil segment 1518 may be formed from the nitinol wires with radiopaque cores. Accordingly, the entire axial length of elongated coil 1504 may be radiopaque.

Figure 16:
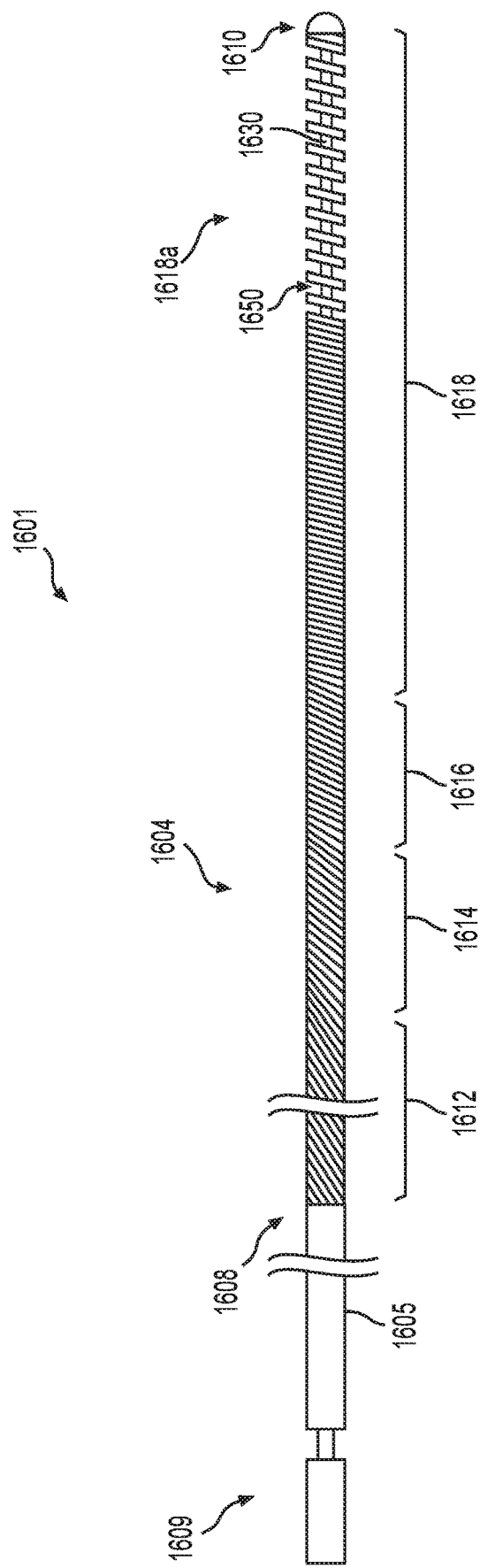
FIG. 16 illustrates an exemplary endovascular device, consistent with various embodiments of the present disclosure.

FIG. 16 illustrates an exemplary endovascular device 1601, according to various embodiments of the present disclosure. Endovascular device 1601 may include an elongated coil 1604 extending between a coil proximal end 1608 and a coil distal end 1610, an elongated sheath 1605 connected to coil proximal end 1608, and a handle 1609 connected to the proximal end of sheath 1605. Handle 1609 may be connected to at least one core wire 1630 extending through sheath 1605 and coil 1604, and configured to control movement (e.g., bending and straightening) of at least a portion of coil 1604. Elongated coil 1604 may be formed from a plurality of helically-wound wires, at least some of which extend from coil proximal end 1608 to coil distal end 1610. Elongated coil 1604 may include a proximal coil segment 1612, a distal coil segment 1618, and at least one transition segment between the proximal and distal coil segments. In the example of FIG. 16, elongated coil 1604 may include two transition segments, a first transition segment 1614 and a second transition segment 1616 situated distally from the first transition segment. However, one of ordinary skill will understand that elongated coil 1604 may include any suitable number of transition segments, with at least one parameter of elongated coil 1604 differing between each segment. For example, elongated coil 1604 may include one transition segment, three transition segments, four transition segments, five transition segments, six transition segments, seven transition segments, eight transition segments, or any other suitable number of transition segments between the proximal and distal coil segments of elongated coil 1604.

In the example of FIG. 16, proximal coil segment 1612 may be formed from six to 16 wires (e.g., ten wires), first transition segment 1614 may be formed from four to nine wires (e.g., six wires), second transition segment 1616 may be formed from three to eight wires (e.g., four wires), and distal coil segment 1618 may be formed from one to four wires (e.g., one wire or two wires). However, as an alternative to, or in addition to, varying the coil angle between the segments of elongated coil 1604 to vary the flexibility between coil segments, spaces 1650 may be formed between the wound wires (i.e., the windings) of coil 1604 in one or more of the coil segments. For example, as shown in FIG. 16, spaces 1650 may be formed between each wire in a distal portion 1618a of distal coil segment 1618, which may advantageously increase the flexibility of distal portion 1618a. In some embodiments, spaces 1650 may be provided along the entire axial length of distal coil segment 1618. Additionally, or alternatively, similar spaces may be provided between the windings in second transition segment 1616, first transition segment 1614, and/or proximal coil segment 1612. In some embodiments, at least a portion of coil 1604 (e.g., proximal coil segment 1612) may lack spaces 1650 between the windings therein to ensure an increase in coil flexibility towards the distal end of coil 1604.

In some embodiments, spaces 1650 between the windings of coil 1604 may be evenly spaced along the longitudinal axis of coil 1604 and may be approximately equal in axial length. In some alternative embodiments, the axial lengths of spaces 1650 may vary along the longitudinal axis of coil 1604, so as to render certain portions of coil 1604 more flexible than other portions of coil 1604. In some embodiments, spaces 1650 may be formed during the process of winding the plurality of wires to form elongated coil 1604 by adding gaps between the wires at a predetermined frequency. In some alternative embodiments, spaces 1650 may be formed by removing one or more wires from the desired portion(s) of elongated coil 1604, e.g., by cutting. Optionally, the wires in proximity to spaces 1650 may be reinforced to maintain spaces 1650 and to hold the wires at their intended coil angle(s), for example, by heat treating the wires to reinforce the wires at their intended coil angle(s). Advantageously, the formation of spaces 1650 within elongated coil 1604 may increase the flexibility of the corresponding section(s) of the coil. For example, spaces 1650 may be formed within a portion or within all of distal coil segment 1618 to form a soft, atraumatic distal tip of endovascular device 1601.

FIG. 17A illustrates an exemplary endovascular device 1701, according to various embodiments of the present disclosure. FIG. 17B illustrates an interior view of endovascular device 1701. Endovascular device 1701 may include an elongated coil 1704 extending between a coil proximal end 1708 and a coil distal end 1710, an elongated sheath 1705 connected to coil proximal end 1708, and a handle 1709 connected to the proximal end of sheath 1705. Handle 1709 may be connected to at least one core wire 1730 extending through sheath 1705 and coil 1704, and configured to control movement (e.g., bending and straightening) of at least a portion of coil 1704. Elongated coil 1704 may be formed from a plurality of helically-wound wires, at least some of which extend from coil proximal end 1708 to coil distal end 1710. Elongated coil 1704 may include a proximal coil segment 1712, a distal coil segment 1718, and at least one transition segment between the proximal and distal coil segments. In the example of FIGS. 17A and 17B, elongated coil 1704 may include two transition segments, a first transition segment 1714 and a second transition segment 1716 situated distally from the first transition segment. However, one of ordinary skill will understand that elongated coil 1704 may include any suitable number of transition segments, with at least one parameter of elongated coil 1704 differing between each segment. For example, elongated coil 1704 may include one transition segment, three transition segments, four transition segments, five transition segments, six transition segments, seven transition segments, eight transition segments, or any other suitable number of transition segments between the proximal and distal coil segments of elongated coil 1704.

In some embodiments, the gauge of the wires forming elongated coil 1704 may vary between the different coil segments such that the flexibility of coil 1704 may differ between segments. In the example shown in FIGS. 17A and 17B, elongated coil 1704 may include a proximal coil segment 1712, a first transition segment 1714, a second transition segment 1716, and a distal coil segment 1718. The wire pitch may be larger in proximal coil segment 1712 than in first transition segment 1714; additionally, or alternatively, the wire pitch may be larger in first transition segment 1714 than in second transition segment 1716; additionally, or alternatively, the wire pitch may be larger in second transition segment 1716 than in distal coil segment 1718. In some embodiments, the outer diameter of elongated coil 1704 may remain substantially constant between coil proximal end 1708 and coil distal end 1710. In some embodiments, to achieve a desired flexibility of elongated coil 1704, the variable wire gauge of elongated coil 1704 may be provided in addition to a variation of the coil angle between the segments of elongated coil 1704 (for example, as shown in FIGS. 12A-12E) and/or in addition to adding spaces between the windings in some or all of the segments of elongated coil 1704 (for example, as shown in FIG. 16).

Advantageously, decreasing the wire gauge may increase the flexibility of the corresponding section of coil 1704;

thus, distal coil segment 1718 may have the smallest wire gauge and may accordingly be the most flexible segment of elongated coil 1704. In addition, proximal coil segment 1712 may have the largest wire gauge and may accordingly be the most rigid segment of elongated coil 1704.

In another embodiment, a first portion of elongated coil 1704 may have a wire pitch of between approximately 1.2 mm and 1.6 mm. A second portion of elongated coil 1704 that is distal to the first portion may have a wire pitch of between approximately 0.50 mm and 0.56 mm. A third portion of elongated coil 1704 that is distal to the second portion may have a wire pitch of between approximately 0.30 mm and 0.34 mm. A fourth portion of elongated coil 1704 that is distal to the third portion may have a wire pitch of between approximately 0.145 mm and 0.165 mm. Optionally, a fifth portion of elongated coil 1704 that is distal to the fourth portion may have a wire pitch of between approximately 0.2 mm and 0.3 mm.

Figure 18A:
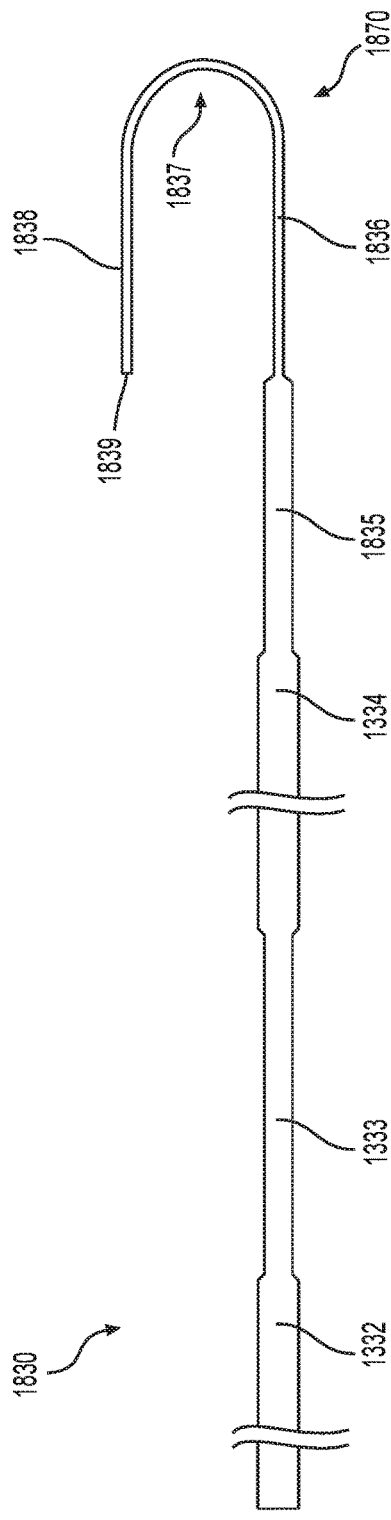
FIG. 18A illustrates an exemplary core wire of an endovascular device, consistent with various embodiments of the present disclosure.

FIG. 18A illustrates an exemplary core wire 1830 of an endovascular device. Core wire 1830 may include core wire zones 1332, 1333, and 1334, as depicted in FIG. 13A, as well as a core wire zone 1835 distal to core wire zone 1334. Core wire zone 1835 may have the same or a similar non-circular cross-section as core wire zone 1333 and an axial length of between approximately 20 mm and 30 mm (e.g., an axial length of approximately 26 mm). In some embodiments, core wire zone 1835 may have a shorter axial length than core wire zone 1333, and approximately 400 mm of the core wire 1830 may be provided between the distal end of core wire zone 1835 and the distal end of core wire zone 1333.

As illustrated in FIG. 18A, core wire 1830 may additionally include a distal end portion 1870, which may be adjacent to core wire zone 1835 and may extend to, and include, the distal tip 1839 of the core wire. The core wire distal end portion 1870 may have an axial length of between approximately 30 mm and 50 mm (e.g., an axial length of approximately 40 mm). In some embodiments, the height of core wire 1830 may be smaller in core wire distal end portion 1870 than in any other portion of the core wire. In some embodiments, the core wire distal end portion 1870 may have a smaller cross-sectional area than the rest of the core wire.

Although the core wire distal end portion 1870 is depicted in FIG. 18A as including a bend 1837, the core wire 1830 (including core wire distal end portion 1870) may be biased in a straightened configuration. In some embodiments, core wire distal end portion 1870 may be flexible such that core wire distal end portion 1870 may be bent or doubled back to form a core wire bend 1837, at which the core wire 1830 may change from a distal axial direction (e.g., to the right in FIG. 18A) to a proximal axial direction (e.g., to the left in FIG. 18A). The core wire distal end portion 1870 may include a first loop portion 1836 extending between core wire zone 1835 and bend 1837 and a second loop portion 1838 extending between bend 1837 and distal tip 1839. In the configuration of FIG. 18A, the core wire bend 1837 may be formed such that first loop portion 1836 and second loop portion 1838 may have approximately equal axial lengths. For example, first loop portion 1836 and second loop portion 1838 may both have an axial length of approximately 20 mm.

Figure 18B:
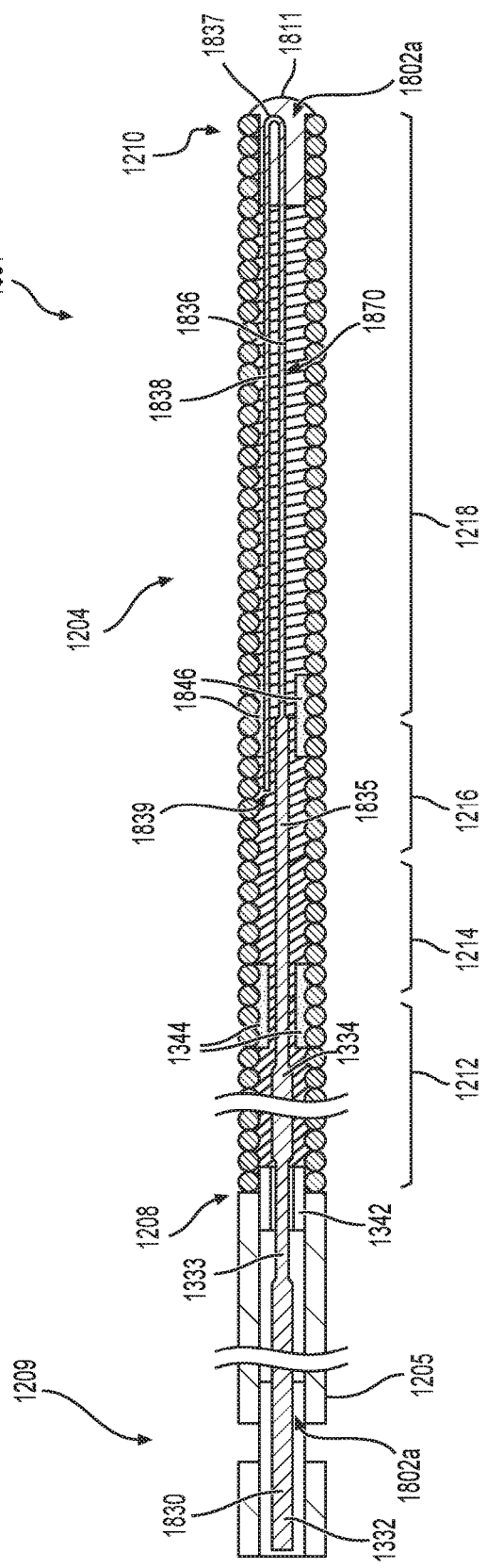
FIG. 18B illustrates an interior view of an endovascular device that includes the core wire of FIG. 18A, consistent with various embodiments of the present disclosure.

FIG. 18B illustrates an interior view of an endovascular device 1801 that includes core wire 1830. Endovascular device 1801 may include handle 1209, elongated sheath 1205, and elongated coil 1204, as depicted in FIG. 13A; elongated coil 1204 depicted in FIG. 18B may include a proximal coil segment 1212, a first transition segment 1214, a second transition segment 1216, and a distal coil segment 1218. FIG. 18B illustrates endovascular device 1801 in a straightened configuration with core wire 1830 extending through an inner channel 1802a that runs between the proximal end of elongated sheath 1205 and the coil distal end 1210. Inner channel 1802a may be formed by the inner lumens of elongated sheath 1205 and coil 1204. As shown in FIG. 18B, core wire 1830 may be situated within endovascular device 1801 in the bent configuration illustrated in FIG. 18A. The proximal end of core wire 1830 may be secured to a portion of handle 1209. Core wire 1830 may extend through the inner channel 1802a to a location at or near the coil distal end 1210; as a result, the core wire distal end portion 1870 may be situated at least partially within the distal coil segment 1218. In some embodiments, core wire 1830 may be situated within the endovascular device 1801 such that the core wire bend 1837 may be situated at or near the coil distal end 1210. Accordingly, the core wire bend 1837 may constitute the distal-most portion of the core wire 1830. The second loop portion 1838 may extend proximally from the core wire bend 1837 so that the core wire distal tip 1839 may be situated proximally from bend 1837 and from the coil distal end 1210. In some embodiments, the core wire bend 1837 may be encompassed within a dome cap 1811, which may be constructed of epoxy and may be rounded to prevent injury to tissue. Dome cap 1811 may be formed, in part, by filling the inner channel 1802a with epoxy near the coil distal end 1210, such that the epoxy covers the core wire bend 1837 and contacts the walls of the inner channel 1802a. Accordingly, dome cap 1811 may bond the core wire bend 1837 to the coil distal end 1210.

As shown in FIG. 18B, at least a portion of the core wire distal end portion 1870 may be situated within the distal coil segment 1218. Accordingly, the first loop portion 1836 and second loop portion 1838 of the core wire may both extend at least partially through distal coil segment 1218. In some embodiments, the core wire distal end portion 1870 (including first loop portion 1836 and second loop portion 1838) may have a height of between approximately 0.030 mm and 0.040 mm. For example, the core wire distal end portion 1870 may have a height of approximately 0.036 mm. Additionally, or alternatively, the core wire distal end portion 1870 may have a width of between approximately 0.05 mm and 0.15 mm. For example, the core wire distal end portion 1870 may have a width of approximately 0.11 mm.

In some embodiments, a movement restrictor 1846 may be provided within the distal coil segment 1218 to prevent axial rotation of the core wire 1830 relative to the coil 1204 without preventing relative axial movement between the core wire 1830 and the coil 1204. For example, a movement restrictor 1846 with a similar configuration as the adhesive or bonding material 1344 depicted in FIG. 13A may be provided at least partially within the distal coil segment 1218 as an anti-rotation mechanism. The movement restrictor 1846 may include a polymer (e.g., PEEK), an adhesive, a weld, and/or any other suitable material. The material of movement restrictor 1846 may be inserted through coil 1204 and may be situated at least partially within inner channel 1802a; accordingly, movement restrictor 1846 may form a narrowing of inner channel 1802a. In the configuration of FIG. 18B, first loop portion 1836 of the core wire may be situated in the center of the inner channel 1802a, such that the first loop portion 1836 is not in contact with the distal coil segment 1218 or movement restrictor 1846. Second loop portion 1838 may be situated in closer proximity to distal coil segment 1218 and at least one surface of second loop portion 1838 may be positioned against, and in contact with, the movement restrictor 1846. In some embodiments, movement restrictor 1846 may protrude into inner channel 1802a to form a step, with the at least one surface of the second looped portion 1838 configured to be positioned against the step. The movement restrictor 1846 may bond the second loop portion 1838 of the core wire to a wall of inner channel 1802a, thus preventing relative axial and rotational movement between the coil 1204 and second loop portion 1838 and distal tip 1839. Thus, movement restrictor 1846 may be configured both as an anti-rotation mechanism for core wire 1830 and as a bond between the second loop portion 1838 and the distal coil segment 1218. Because the second loop portion 1838 of the core wire may extend proximally beyond the movement restrictor 1846, the bond between the core wire and the wall of inner channel 1802a may be situated distally from distal tip 1839 of the core wire.

In some alternative embodiments, movement restrictor 1846 may include an insert situated within inner channel 1802a. For example, movement restrictor 1846 may have a similar configuration as internal connector 1342, as depicted in FIG. 13A, or another ring-shaped insert and may be connected to the wall of inner channel 1802a. Additionally, or alternatively, the insert of movement restrictor 1846 may be configured as a partial obstruction within elongated coil 1204 that is connected to the wall of inner channel 1802a.

Figure 18C:
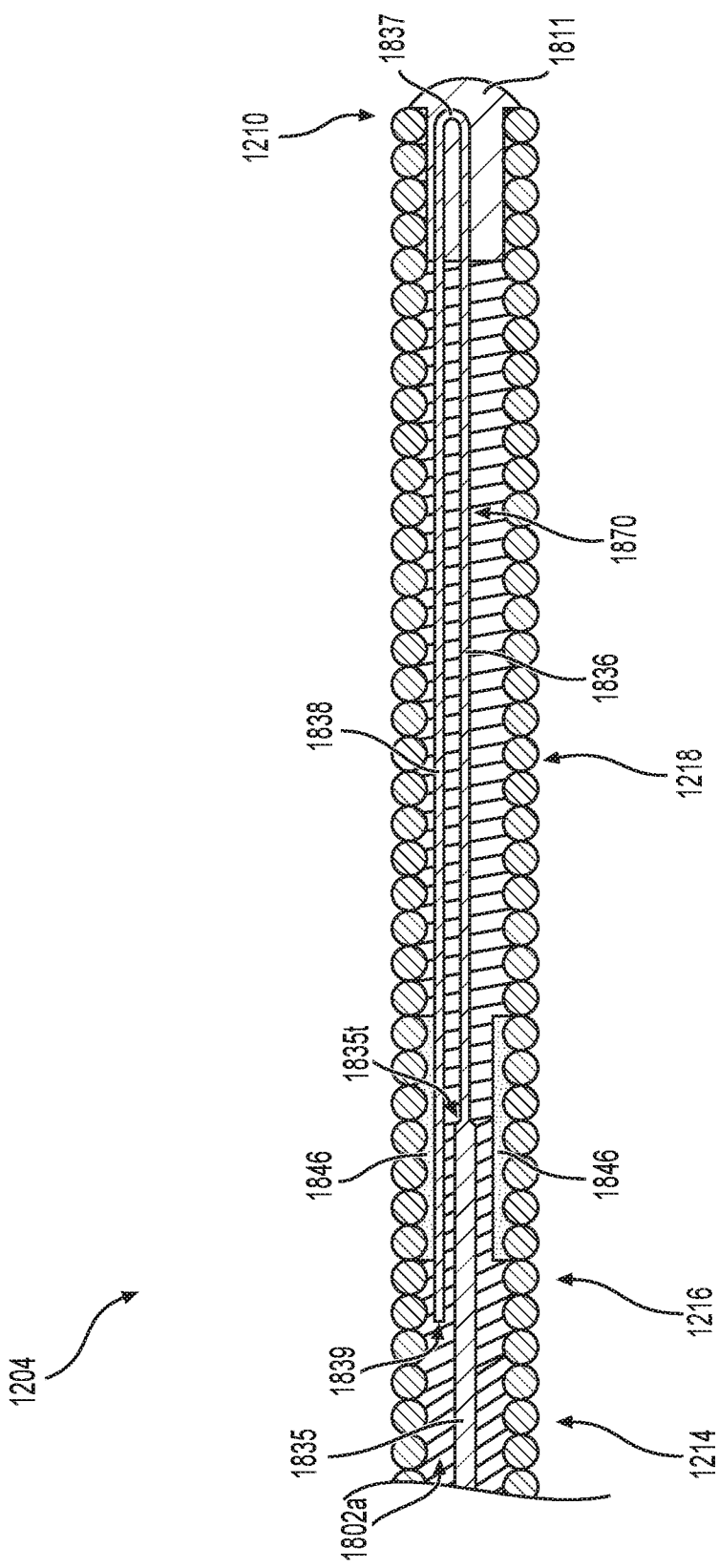
FIG. 18C illustrates an enlarged view of a distal portion of the endovascular device of FIG. 18B in a straightened configuration, consistent with various embodiments of the present disclosure.

FIG. 18C illustrates an enlarged view of a distal portion of the endovascular device 1801 in the straightened configuration. Core wire 1830 may be bonded to coil 1204 by dome cap 1811 and by movement restrictor 1846; apart from these two points of connection, core wire 1830 may be configured for movement relative to coil 1204. As shown in FIG. 18C, second loop portion 1838 of the core wire may be provided between first loop portion 1836 and distal coil segment 1218. However, when endovascular device 1801 is in the straight configuration depicted in FIG. 18C, second loop portion 1838 may be spaced apart from distal coil segment 1218 such that a gap may be provided between the second loop portion 1838 and the walls of inner channel 1802a. Movement restrictor 1846 and dome cap 1811 may both extend between coil 1204 and core wire 1830, thus bonding the coil and core wire together. In some embodiments, core wire bend 1837 may be situated evenly with the distal end 1210 of the coil. Alternatively, core wire bend 1837 may be situated proximally from coil distal end 1210.

As shown in FIG. 18C, the second loop portion 1838 may extend proximally beyond movement restrictor 1846. As a result, distal tip 1839 of the core wire may be situated proximally from movement restrictor 1846. Alternatively, distal tip 1839 may be placed in contact with movement restrictor 1846. In some embodiments, the transition 1835t between core wire zone 1835 and the core wire distal end portion 1870 may be situated between the proximal and distal ends of movement restrictor 1846 while endovascular device 1801 is in the straight configuration depicted in FIG. 18C. In addition, gaps may be formed between the wall of inner channel 1802a and the first loop portion 1836 and second loop portion 1838. That is, apart from the connections between core wire 1830 and coil 1204 formed by movement restrictor 1846 and dome cap 1811, the rest of core wire distal end portion 1870 may be spaced apart from the walls of inner channel 1802a when the endovascular device is in the straight configuration.

Figure 18D:
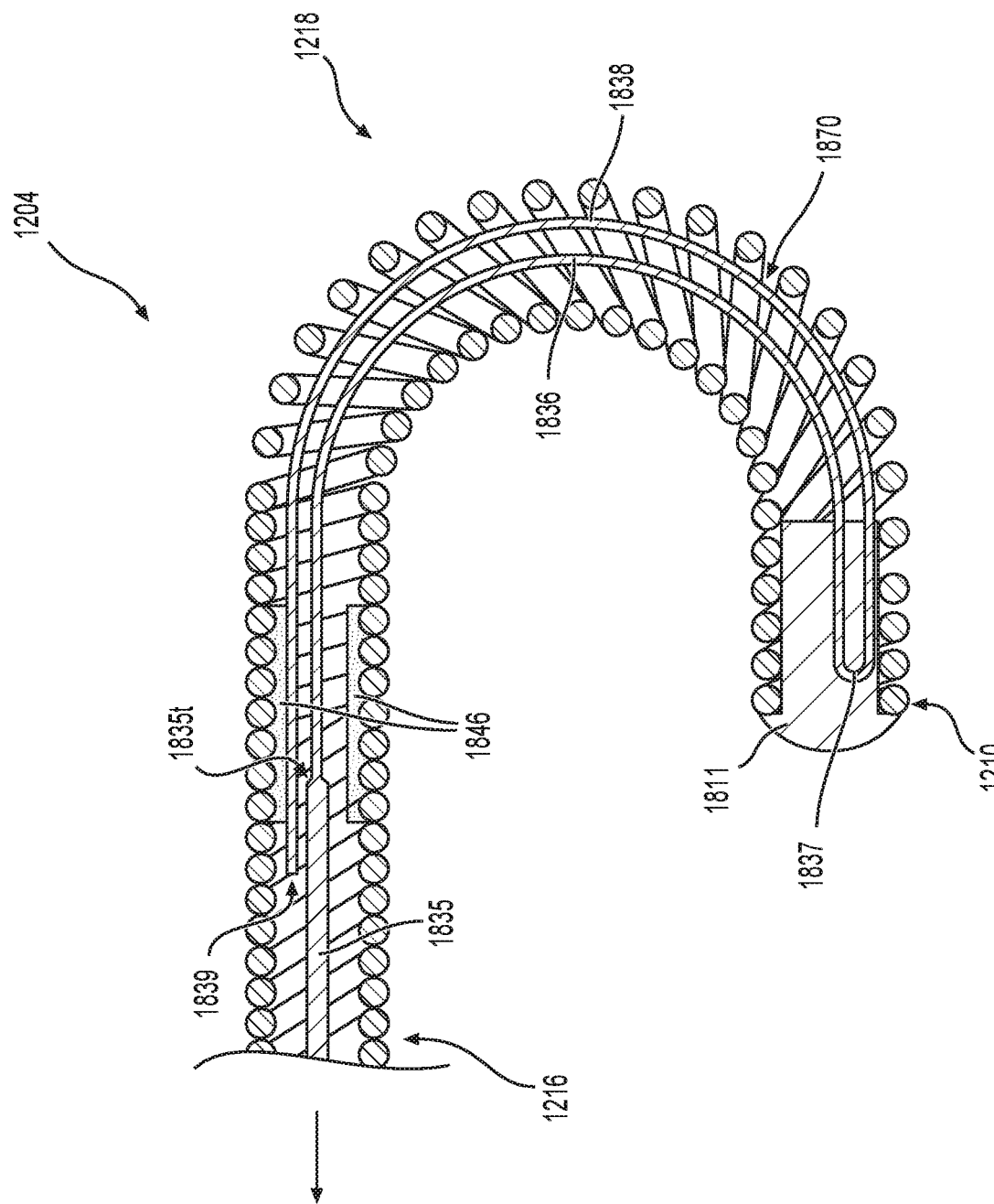
FIG. 18D illustrates the endovascular device distal portion of FIG. 18C in a curved configuration, consistent with various embodiments of the present disclosure.

FIG. 18D illustrates the distal portion of endovascular device 1801 in a curved configuration. The curved configuration of FIG. 18D may be effected by application of a proximally-directed force on core wire 1830 (which may be caused, for example, by proximal movement of user actuation segment 1222 relative to elongated sheath 1205). Due to its relatively small cross-sectional area, core wire distal end portion 1870 may have a lower moment of inertia relative to the rest of the core wire. As a result, axially-directed force application on core wire 1830 may cause first loop portion 1836 and second loop portion 1838 of the core wire to buckle from their respective straightened configurations into curved configurations, without other portions of core wire 1830 buckling. Due to the bonds between core wire distal end portion 1870 and coil 1204 that are formed by dome cap 1811 and by movement restrictor 1846, buckling of first loop portion 1836 and second loop portion 1838 may force the distal portion of coil 1204 to radially bend from the straight configuration of FIG. 18C into the curved configuration of FIG. 18D. In some embodiments, movement restrictor 1846 may be configured as a hinge of core wire distal end portion 1870 by permitting rotation of second loop portion 1838 but preventing axial movement of second loop portion 1838. As a result, first loop portion 1836 and second loop portion 1838 may buckle under lower applied axial forces, compared to a configuration in which the end of second loop portion 1838 was fixed against rotation. Advantageously, the hinge of movement restrictor 1846 may improve steerability of coil distal end 1210 by reducing the magnitude of force needed to cause bending of the distal end of endovascular device 1801.

In some embodiments, the entire length of coil 1204 distal to movement restrictor 1846 may bend due to axial force application on core wire 1830. As a result, some or all of distal coil segment 1218 may be configured to bend due to axial force application on core wire 1830. Dome cap 1811 may secure core wire bend 1837 against movement relative to coil distal end 1210. Similarly, movement restrictor 1846 may secure the portion of second loop portion 1838 that is in contact with movement restrictor 1846 against movement relative to the portion of coil 1204 that is in contact with movement restrictor 1846. However, the sections of first loop portion 1836 and second loop portion 1838 between dome cap 1811 and movement restrictor 1846 may freely move within coil 1204 and may buckle or otherwise distort within coil 1204 when a force is applied to core wire 1830. In addition, and as illustrated in FIG. 18D, the proximal movement of core wire 1830 may pull core wire transition 1835t in a proximal direction relative to coil 1204. In some embodiments, core wire distal end portion 1870 may be configured such that repeated exertions of force on core wire 1830 (e.g., pulling core wire 1830 in a proximal direction) may result in consistent directional flexing of the core wire 1830. This may be due to the bonds between core wire 1830 and coil 1204 that are formed by dome cap 1811 and movement restrictor 1846, as well as to the non-circular cross-sectional shape of core wire distal end portion 1870. Specifically, due to the aforementioned shape and the placement of core wire distal end portion 1870 within coil 1204, core wire distal end portion 1870 may preferentially bend into the configuration depicted in FIG. 18D when an axially-directed force is exerted on core wire 1830.

Advantageously, looped core wire 1830 may reduce the magnitude of force required to effect bending of the distal end of endovascular device 1801. Specifically, the low moment of inertia of core wire distal end portion 1870, combined with the hinge of movement restrictor 1846 and the arrangement of core wire portions 1836 and 1838 within coil distal segment 1218, may enable core wire distal end portion 1870 to buckle (and, thus, enable bending of endovascular device 1801) under the application of less than half the force that is required to bend endovascular devices known in the art that do not incorporate a looped core wire. As a result, the looped core wire 1830 may provide more exact steering of the distal end of endovascular device 1801, since less force is required to bend the distal end of endovascular device 1801 into a desired curved configuration. In addition, endovascular device 1801 may have a soft, atraumatic tip due to the coil arrangement in distal coil segment 1218 and the configuration of dome cap 1811 as a rounded, atraumatic edge of endovascular device 1801. Accordingly, endovascular device 1801 may be easily maneuvered through narrow, tortuous lumens of the body (such as intracranial vessels) due to the improved steering provided by looped core wire 1830, without causing injury to the surrounding anatomy.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. While certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An intravascular device, comprising:
    an elongated sheath having a proximal end and a distal end, the elongated sheath being sized and configured to traverse human vasculature; and
    an elongated coil secured relative to the distal end of the elongated sheath, the elongated coil extending between a proximal end of the coil and a distal end of the coil to define a longitudinal axis, wherein the elongated coil comprises:
    a first coil segment formed from a plurality of wires, wherein the plurality of wires of the first coil segment are helically-wound in the first coil segment at a first coil angle relative to the longitudinal axis,
    a second coil segment distal to the first coil segment, the second coil segment formed from a first subset of the plurality of wires, the first subset including some but not all of the plurality of wires, wherein the first subset of wires is helically-wound in the second coil segment at a second coil angle that is larger than the first coil angle, and
    a third coil segment distal to the second coil segment, the third coil segment formed from a second subset of the plurality of wires, the second subset including some but not all of the first subset of the plurality of wires, wherein the second subset of wires is helically-wound in the third coil segment at a third coil angle that is larger than the first coil angle and the second coil angle,
    wherein the first coil segment, the second coil segment, and the third coil segment are configured such that flexibility of the elongated coil increases in a longitudinal direction toward the distal end of the elongated coil;
    wherein a cross section of the first coil segment perpendicular to the longitudinal axis contains all of the plurality of wires;
    wherein a cross section of the second coil segment perpendicular to the longitudinal axis contains all of the first subset of the plurality of wires; and
    wherein a cross section of the third coil segment perpendicular to the longitudinal axis contains all of the second subset of the plurality of wires.

2. The intravascular device of claim 1, wherein the plurality of wires comprises between six wires and 16 wires, the first subset of wires comprises between three wires and eight wires, and the second subset of wires comprises one wire or two wires.

3. The intravascular device of claim 2, wherein the plurality of wires comprises ten wires, the first subset of wires comprises four wires, and the second subset of wires comprises two wires.

4. The intravascular device of claim 1, wherein the first coil angle is between 55° and 65°, the second coil angle is between 65° and 75°, and the third coil angle is between 75° and 85°.

5. The intravascular device of claim 1, wherein the wires of the second subset of wires are constructed at least partially of a first material and the remaining wires of the plurality of wires are constructed of a second material that is different from the first material.

6. The intravascular device of claim 5, wherein wires extending to the distal end of the elongated coil are constructed at least partially from the first material.

7. The intravascular device of claim 1, wherein at least one wire of the plurality of wires has a distal end that is situated proximally from the distal end of the elongated coil.

8. The intravascular device of claim 1, further comprising:
    a fourth coil segment situated between the first coil segment and the second coil segment, the fourth coil segment formed from a third subset of the plurality of wires that includes more wires than the first and second subsets of wires, wherein the third subset of wires is helically-wound in the fourth coil segment at a fourth coil angle that is larger than the first coil angle and smaller than the second coil angle.

9. The intravascular device of claim 8, wherein the third subset of wires comprises between four wires and nine wires.

10. The intravascular device of claim 9, wherein the third subset of wires comprises six wires.

11. The intravascular device of claim 8, wherein the third coil segment has a greater axial length than the second coil segment and the fourth coil segment.

12. The intravascular device of claim 8, wherein the fourth coil angle is between 55° and 65°.

13. The intravascular device of claim 8,
wherein the first coil segment, second coil segment, and third coil segment are configured to have differing flexibilities, and
wherein the first coil segment, the second coil segment, and the third coil segment are aligned axially along the elongated coil to form a unified structure of the elongated coil that has axially variable flexibility.

14. The intravascular device of claim 1, wherein spaces are formed between windings of the elongated coil in a first region of the elongated coil.

15. The intravascular device of claim 14, wherein the first region of the elongated coil is situated within the third coil segment and extends axially to the distal end of the elongated coil, the spaces between the windings being spaced at a regular interval between windings.

16. The intravascular device of claim 1, wherein a wire gauge of the elongated coil decreases toward the distal end of the elongated coil.

17. The intravascular device of claim 1, wherein material composition of the elongated sheath varies toward the distal end of the elongated sheath.

18. The intravascular device of claim 1, further comprising:
an elongated core wire arranged at least partially within the elongated sheath and configured such that when the elongated core wire is moved axially, the distal end of the elongated coil bends radially,
wherein the elongated core wire is doubled back in a loop within the elongated coil such that a terminal distal end of the elongated core wire is spaced from the distal end of the elongated coil.

19. The intravascular device of claim 18, further comprising:
a movement restrictor situated at least partially within the elongated coil, the movement restrictor being configured to limit axial movement of the terminal distal end of the elongated core wire in at least one axial direction relative to the elongated coil and to permit the loop of the elongated core wire to buckle, resulting in a bend in the distal end of the elongated coil, when an axial force is exerted on the elongated core wire.

* * * * *